United States Patent [19]

Bowler et al.

[11] 4,000,305
[45] Dec. 28, 1976

[54] 15-, 16- AND 17-INDOLYL OR INDOLINYL NOR PROSTANOIC ACID DERIVATIVES

[75] Inventors: Jean Bowler; Keith Blakeney Mallion; Dora Nellie Richardson, all of Macclesfield, England

[73] Assignee: Imperial Chemical Industries Limited, London, England

[22] Filed: Oct. 1, 1975

[21] Appl. No.: 618,676

Related U.S. Application Data

[63] Continuation-in-part of Ser. No. 397,327, Sept. 14, 1973, Pat. No. 3,931,206.

[30] Foreign Application Priority Data

Sept. 27, 1972 United Kingdom ............ 44652/72

[52] U.S. Cl. .......................... 424/274; 260/240 R
[51] Int. Cl.$^2$ ............ C07D 209/04; C07D 209/12
[58] Field of Search ... 260/240 R, 468 D, 326.11 R, 260/326.13 R, 326.16; 424/274

[56] References Cited

UNITED STATES PATENTS

| | | | |
|---|---|---|---|
| 3,821,279 | 6/1974 | Kurono et al. | 260/240 RX |
| 3,872,107 | 3/1975 | Crabbe | 260/240 RX |
| 3,903,131 | 9/1975 | Magerlein | 260/240.1 X |

*Primary Examiner*—Allen B. Curtis
*Attorney, Agent, or Firm*—Cushman, Darby & Cushman

[57] ABSTRACT

This invention relates to novel 15-, 16- and 17-heterocyclyl nor-prostanoic acid derivatives, for example 9α,11α,15-trihydroxy-16-(indol-5-yloxy)-17,18,19,20-tetranor-5-cis, 13-trans-prostadienoic acid, which have a unique profile of Prostaglandin-like properties, and to processes for their manufacture, and also to pharmaceutical or veterinary compositions containing one of said novel derivatives, and a method of inducing luteolysis in an animal host by administering one of said novel derivatives.

7 Claims, No Drawings

15-, 16- AND 17-INDOLYL OR INDOLINYL NOR PROSTANOIC ACID DERIVATIVE

This application is a continuation-in-part of Ser. No. 397,327, filed Sept. 14, 1973, now U.S. Pat. No. 3,931,206.

This invention relates to prostanoic acid derivatives and in particular it relates to prostanoic acid derivatives which possess luteolytic activity. The new compounds are therefore advantageous when used as contraceptives, for the induction of labour or termination of pregnancy, or for control of the oestrus cycle, and are also useful as hypotensives or for the relief of bronchospasm, and as inhibitors of blood platelet aggregation or of gastric secretion. The new compounds are also useful for addition to semen intended for artificial insemination of domestic animals, the success rate of insemination being thereby increased, especially in pigs and cattle.

The compounds described in this specification will be named as derivatives of prostane of the formula shown below and numbered as shown:

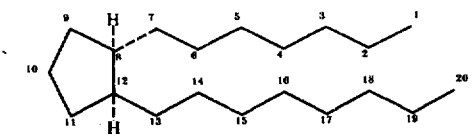

According to the invention there is provided a prostanoic acid derivative of the formula:

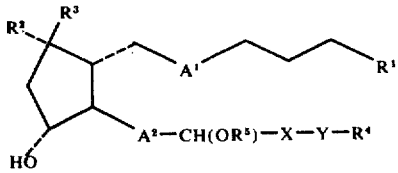

wherein $R^1$ is a hydroxymethyl or carboxy radical, an alkoxycarbonyl or alkoxymethyl radical each of 2 to 11 carbon atoms, or an alkoxycarbonyl radical of 2 or 3 carbon atoms which bears as substituent a $\beta$- or $\gamma$-dialkylamino radical wherein each alkyl radical is of 1 to 4 carbon atoms, or a $\beta$- or $\gamma$-(1-pyrrolidinyl), -piperidino or -morpholino radical; either $R^2$ is a hydroxy radical or an alkanoyloxy radical of 1 to 4 carbon atoms and $R^3$ is a hydrogen atom, or $R^2$ and $R^3$ together form an oxo radical; $A^1$ is an ethylene or a vinylene radical; $A^2$ is an ethylene or trans-vinylene radical; either X is an alkylene radical of 1 to 3 carbon atoms bearing as substituents 0, 1 or 2 alkyl radicals, each of 1 to 3 carbon atoms and Y is an oxygen or sulphur atom, a sulphinyl, sulphonyl, imino or alkylimino (-NAlkyl-) radical of up to 4 carbon atoms, or a direct bond; or X and Y are each a direct bond; $R^4$ is a radical derived from a heterocyclic compound which is an aromatic 5- or 6- membered ring containing one or two non-adjacent nitrogen heteroatoms from an aromatic fused benzo-homologue thereof, or from indoline or pyridazine, which radical is unsubstituted or is substituted with 1 to 4 substituents selected from halogen atoms or alkyl or alkoxy radicals each of 1 to 5 carbon atoms; $R^5$ is a hydrogen atom or an alkyl radical of 1 to 5 carbon atoms, and which prostanoic acid derivative is further unsubstituted or bears an alkyl substituent of 1 to 4 carbon atoms on carbon atom 2, 3 or 4 thereof; and for those compounds wherein $R^1$ is a carboxy radical the pharmaceutically or veterinarily acceptable base addition salts thereof; and for those compounds wherein $R^1$ is a carboxy radical and $R^2$ is the hydroxy radical the 1 9$\alpha$-lactones thereof.

A suitable value for $R^1$ when it is an alkoxycarbonyl radical of 2 to 11 carbon atoms is, for example, a methoxycarbonyl, ethoxycarbonyl, n-butoxycarbonyl or n-decyloxycarbonyl radical, and a suitable value for $R^1$ when it is an alkoxymethyl radical of 2 to 11 carbon atoms is, for example, a methoxymethyl, ethoxymethyl or butoxymethyl radical.

A suitable value for $R^2$ when it is an alkanoyloxy radical of 1 to 4 carbon atoms is, for example, an acetoxy or propionyloxy radical.

A suitable value for X when it is an alkylene radical of 1 to 3 carbon atoms bearing as substituents 0, 1 or 2 alkyl radicals, each of 1 to 3 carbon atoms is, for example a methylene, ethylene or trimethylene radical bearing 0, 1 or 2 methyl substituents, for example a methylene, ethylidene, isopropylidene or trimethylene radical.

A suitable value for Y when it is an alkyleneimino radical of up to 4 carbon atoms is, for example, a methylimino radical.

A suitable value for $R^4$ when it is a radical derived from a 5-membered heterocyclic ring or a fused benzo-homologue thereof is, for example, a pyrrolyl, imidazolyl, indolyl or benzimidazolyl radical, and a suitable value for $R^4$ when it is a radical derived from a 6-membered heterocyclic ring or a fused benzo-homologue thereof is, for example, a pyridyl, pyrimidinyl, pyrazinyl, quinolyl, isoquinolyl, quinazolinyl or quinoxalinyl radical.

Suitable halogen substituents in $R^4$ are, for example chlorine, bromine, iodine and fluorine atoms, and suitable alkyl and alkoxy substituents in $R^4$ are, for example, methyl, ethyl, propyl, methoxy and ethoxy radicals.

A suitable value for $R^5$ when it is an alkyl radical is, for example, a methyl, ethyl or propyl radical.

A suitable value for the alkyl radical of up to 4 carbon atoms which may be present as a substituent on carbon atom 2, 3 or 4 is, for example a methyl or ethyl radical.

Examples of base-addition salts are the ammonium, alkyl-ammonium containing 1 to 4 alkyl radicals each of 1 to 6 carbon atoms, alkanolammonium containing 1 to 3 2-hydroxyethyl radicals, and alkali metal salts, for example the triethylammonium, ethanolammonium, diethanolammonium, sodium and potassium salts.

It will be observed that the compounds of the formula I contain at least four asymmetric carbon atoms, namely carbon atoms 8, 11, 12 and 15, the configurations at three of which, 8, 11 and 12 are specified in formula I, and that carbon atoms 2, 3, 4, 9 and 15 may also be asymmetrically substituted, so that it is clear that such compounds can exist in at least two optically active forms. It is to be understood that the useful properties of the racemate may be present to differing extents in the optical isomers, and that this invention relates to the racemic form of the compounds of formula I and any optically active form which shows the above useful properties, it being a matter of common general knowledge how the optically active forms may be obtained, and to determine their respective biological properties.

It is also to be understood that the above definition encompasses both C-15 epimers.

More particularly, the invention provides a prostanoic acid derivative of the formula I wherein $R^1$ is a carboxy or hydroxymethyl radical or an alkoxycarbonyl radical of 1 to 4 carbon atoms, $A^1$ and $A^2$ have the meanings defined above, $R^2$ is a hydroxy radical and $R^3$ is a hydrogen atom or $R^2$ and $R^3$ together form an oxo radical, either X is a methylene radical and Y is an oxygen atom, or X is a methylene or ethylene radical and Y is a direct bond, or X and Y are each a direct bond, $R^4$ is an indolyl, benzimidazolyl, pyridyl, pyrimidinyl, quinolyl, indolinyl or pyridazinyl radical, which radical is unsubstituted or is substituted as defined above, and $R^5$ is a hydrogen atom, and which prostanoic acid derivative is further unsubstituted or bears an alkyl substituent of 1 to 4 carbon atoms on carbon atom 2 thereof, and for those compounds wherein $R^1$ is a carboxy radical, the sodium salts thereof.

Particular values for $R^4$ are unsubstituted indolyl, indolyl bearing 1 or 2 substituents selected from methyl radicals and chlorine and fluorine atoms, methylbenzimidazolyl unsubstituted pyridyl, pyridyl bearing 1 to 4 substituents selected from methyl and methoxy radicals, and chlorine atoms, pyrimidinyl bearing 1 or 2 substituents selected from methyl and methoxy radicals, unsubstituted quinolyl, methylquinolyl, unsubstituted indolinyl, methylindolinyl and chloropyridazinyl radicals.

Preferred compounds of the invention are those compounds wherein X is a methylene radical and Y is an oxygen atom.

A particular group of prostanoic acid derivatives of the invention comprises those compounds of the formula wherein $R^4$ is an indolyl or indolinyl radical, for example a 1-, 2-, 3-, 4- or 5- indolyl or indolinyl radical, and especially those prostanoic acid derivatives of the formula I wherein $R^1$ is a carboxy or hydroxymethyl radical or an alkoxycarbonyl radical of 2 to 5 carbon atoms, for example a methoxycarbonyl radical, $R^2$ is a hydroxy radical and $R^3$ is a hydrogen atom, or $R^2$ and $R^3$ together form an oxo radical, $A^1$ is an ethylene, cis-vinylene or trans-vinylene radical, $A^2$ is an ethylene or trans-vinylene radical, X and Y together form a methylene, ethylene or methyleneoxy radical, or a direct bond, $R^5$ is a hydrogen atom, and $R^4$ is a 1-,2-,3-,4- or 5-indolyl or indolinyl radical which bears 0 to 3 substituents selected from halogen atoms, for example, chlorine, bromine, iodine or fluorine atoms, and alkyl and alkoxy radicals each of 1 to 5 carbon atoms, for example methyl and methoxy radicals, which compounds bear 0 or 1 alkyl substituent of 1 to 4 carbon atoms, for example a methyl radical, on carbon atom 2 thereof, and the pharmaceutically or veterinarily acceptable base addition salts thereof. Particular values for $R^4$ are therefore 2-, 3-, 4- and 5-indolyl, 1-, 3- and 7-methylindol-5-yl, 1,2-dimethylindol-5-yl, 3-chloroindol-5-yl, 7-fluoroindol-5-yl, 1-indolinyl and 1-methylindolin-5-yl radicals. A preferred group of such compounds comprises those compounds of the formula I wherein $R^1$ is a carboxy, hydroxymethyl or methoxycarbonyl radical, $A^1$ is an ethylene, cis-vinylene or trans-vinylene radical, $R^2$ is a hydroxy radical, $R^3$ is a hydrogen atom, $A^2$ is an ethylene or trans-vinylene radical, $R^5$ is a hydrogen atom, X is a methylene radical, Y is an oxygen atom and $R^4$ is 5-indolyl radical, and for those compounds wherein $R^1$ is a carboxy radical, the salts thereof as defined above. Particular preferred compounds in this group are 9α,11α,15-trihydroxy-16-(indol-5-yloxy)-17,18,19,20-tetranor-5-cis, 13-trans-prostadienoic acid, 16-(7-fluorindol-5-yl)-9α,11α,15-trihydroxy-17,18,19,20-tetranor-5-cis,13-trans-prostadienoic acid, methyl 9α,11α,15-trihydroxy-16-(indol-5-yloxy)-17,18,19,20-tetranor-5-cis,13-trans-prostadienoate, 16-(indol-5-yloxy)-17,18,19,20-tetranor-5-cis,13-trans-prostadien-1,9α,11α,15-tetraol, 9α,1-1α,15-trihydroxy-16-(indol-5-yloxy)-2-methyl-17,18,19,20-tetranor-5-cis,13-trans-prostadienoic acid, 9α,11α,15-trihydroxy-16-(indol-5-yloxy)-17,18,19,20-tetranor-13-trans-prostenoic acid, and 9α,11α,15-trihydroxy-16-(indol-5-yloxy)-17,18,19,20-tetranor-5-trans-prostadienoic acid, and the sodium and potassium salts of those compounds which are acids, and particularly preferred indolinyl compounds are 9α,11α,15-trihydroxy-17-(indolin-1-yl)-18,19,20-trinor-5-cis,13-trans-prostadienoic acid, and the sodium and potassium salts thereof.

A further particular group of prostanoic acid derivatives of the invention comprises those compounds of the formula I wherein $R^4$ is a pyridyl radical, and especially those prostanoic acid derivatives of the formula I wherein $R^1$ is a carboxy radical or an alkoxycarbonyl radical of 2 to 5 carbon atoms, for example, a methoxycarbonyl radical, $A^1$ is a cis-vinylene radical, $R^2$ is a hydroxy radical, $R^3$ is a hydrogen atom, $A^2$ is a trans-vinylene radical, $R^5$ is a hydrogen atom, X and Y together form an ethylene or methyleneoxy radical, or a direct bond, and $R^4$ is a 2-, 3- or 4-pyridyl radical bearing 0 to 4 substituents selected from halogen atoms, for example chlorine, bromine or iodine atoms, and alkyl and alkoxy radicals each of 1 to 5 carbon atoms, for example methyl and methoxy radicals, and for those compounds wherein $R^1$ is a carboxy radical, the pharmaceutically or veterinarily acceptable base addition salts thereof. A preferred sub-group of compounds within this group comprises those compounds of the formula I wherein $R^1$ is a carboxy or methoxycarbonyl radical, $A^1$ is a cis-vinylene radical, $R^2$ is a hydroxy radical, $R^3$ is a hydrogen atom, $A^2$ is a trans-vinylene radical, $R^5$ is a hydrogen atom, X is a methylene radical, Y is an oxygen atom, and $R^4$ is an unsubstituted 2-, 3- or 4-pyridyl radical, a chloropyridyl radical wherein the chlorine substituent is located meta to the carbon atom bearing the free valency, a methylpyridyl radical wherein the methyl substituent is located meta or para to the carbon atom bearing the free valency, or a 4, 6-dimethylpyrid-2-yl radical, and for those compounds wherein $R^1$ is a carboxy radical, the salts thereof as defined above. Particular values for $R^4$ are therefore 2-, 3- and 4-pyridyl, 6-methylpyrid-2-yl, 2-, 4- and 6-methylpyrid-3-yl, 4,6-dimethylpyrid-2-yl, 2,6-dimethylpyrid-4-yl, 6-chloropyrid-2-yl, 5-chloropyrid-3-yl, 2-chloropyrid-4-yl, 2,5-dichloropyrid-3-yl, and 6-methoxypyrid-3-yl radicals. Particular preferred compounds in this sub-group are 9α,11α,15-trihydroxy-16-(pyrid-2-yloxy)-17,18,19,20-tetranor-5-cis, 13-trans-prostadienoic acid, 9α, 11α,15-trihydroxy-16-(pyrid-3-yloxy)-17,18,19,20-tetranor-5-cis, 13-trans-prostadienoic acid, methyl 9α, 11α,15-trihydroxy-16-(pyrid-4-yloxy)-17,18,19,20-tetranor-5-cis, 13-trans-prostadienoate, 9α,11α,15-trihydroxy-16-(6-methylpyrid-2-yloxy)-17,18,19,20-tetranor-5-cis, 13-trans-prostadienoic acid, 9α, 11α,15-trihydroxy-16-(6-methylpyrid-3-yloxy)-17,18,19,20-tetranor-5-cis, 13-trans-prostadienoic acid, 16-(6-chloropyrid-2-yloxy) -9α,11α,15-trihydroxy-17,18,19,20-tetranor-5-cis, 13-trans-prostadienoic acid, 16-(2-chloropyrid-4-yloxy)-9α,11α,15-trihydroxy-17,18,19,20-tetranor-5-cis, 13-trans-prostadienoic acid, methyl 16-(5-chloropyrid-3-yloxy)-9α,11α,15-trihydroxy-17,18,19,20-tetranor-5-cis, 13-trans-prostadienoate and methyl 16-(4,6-dimethylpyrid-2-yloxy)-9α,11α,15-trihydroxy-17,18,19,20-tetranor-5-cis, 13-trans-prostadienoate, and the sodium and potassium salts of those compounds which are acids.

A further particular group of prostanoic acid derivatives of the invention comprises those compounds of the formula I wherein $R^1$ is a carboxy radical or an alkoxycarbonyl radical of 2 to 5 carbon atoms, for example a methoxycarbonyl radical, $A^1$ is a cis-vinylene radical, $R^2$ is a hydroxy radical, $R^3$ is a hydrogen atom, $A^2$ is a trans-vinylene radical, $R^5$ is a hydrogen atom, X and Y together form a methyleneoxy radical or a direct bond, and $R^4$ is a pyrimidinyl, quinolyl or benzimidazolyl radical, bearing 0 to 3 substituents selected from alkyl and alkoxy radicals each of 1 to 5 carbon atoms, for example, methyl and methoxy radicals, and the pharmaceutically or veterinarily acceptable base addition salts thereof. Suitable values for $R^4$ are, for example, 2-pyrimidinyl,2-, 3- and 7-quinolyl and 2-benzimidazolyl radicals. Particular values for $R^4$ are therefore 4-methoxy-6-methyl-2-pyrimidinyl, 4-methyl-2-quinolyl, 3-quinolyl, 6-quinolyl, and 1-methyl-2-benzimidazolyl radicals. Particular preferred compounds in this group are 9α,11α,15-trihydroxy-16-(quinol-3-yloxy)-17,18,19,20-tetranor-5-cis, 13-trans-prostadienoic acid and 9α,11α,15-trihydroxy-15-(1-methylbenzimidazol-2-yl)-16,17,18,19,20-pentanor-5-cis, 13-trans-prostadienoic acid.

A further particular group of prostanoic acid derivatives of the invention comprises those compounds of the formula I wherein $R^1$ is a carboxy radical or an alkoxycarbonyl radical of 2 to 5 carbon atoms, for example a methoxycarbonyl radical, $A^1$ is a cis-vinylene radical, $R^2$ is a hydroxy radical, $R^3$ is a hydrogen atom, $A^2$ is a trans-vinylene radical, $R^5$ is a hydrogen atom, X and Y together form a methyleneoxy radical and $R^4$ is a pyridazinyl radical, for example a 3-pyridazinyl radical, for example a 6-chloropyridazin-3-yl radical, and for those compounds wherein $R^1$ is a carboxy radical, the pharmaceutically or veterinarily acceptable salts thereof. A preferred compound in this group is 16-(6-chloropyridazin-3-yloxy)-9α,11α,15-trihydroxy-17,18,19,20-tetranor-5-cis, 13-trans-prostadienoic acid.

The prostanoic acid derivatives of the invention may be manufactured by methods known in themselves for the manufacture of chemically analogous compounds. Thus, the following processes for the manufacture of the cyclopentane derivative of the formula I, are provided as further features of the invention:

a. for those compounds wherein $R^1$ is a carboxy radical, and $R^5$ is a hydrogen atom, the hydrolysis of a compound of the formula:

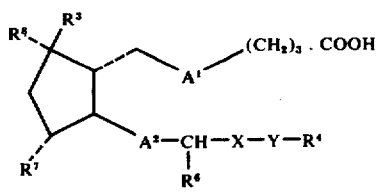

or of a mixed anhydride thereof, wherein $A^1$, $A^2$, X, Y and $R^4$ have the meanings stated above, either $R^8$ is a hydroxy radical and $R^3$ is a hydrogen atom or $R^8$ and $R^3$ together form an oxo radical, and $R^6$ and $R^7$ are each a tetrahydropyran-2-yloxy radical or an acyloxy radical of 1 to 6 carbon atoms, or $R^3$ is a hydrogen atom, $R^8$ is an acyloxy radical of up to 15 carbon atoms, $R^7$ is a hydroxy radical or an acyloxy radical of up to 15 carbon atoms and $R^6$ is a hydroxy radical, which compound II bears 0 or 1 alkyl substituent of 1 to 4 carbon atoms on carbon atom 2, 3 or 4, whereafter when a salt is required the product is reacted with a base; or b. for those compounds wherein $R^1$ is a carboxy radical, $R^2$ is a hydroxy radical and $R^3$ is a hydrogen atom, and $A^1$ is a vinylene radical, the reaction of a lactol of the formula:

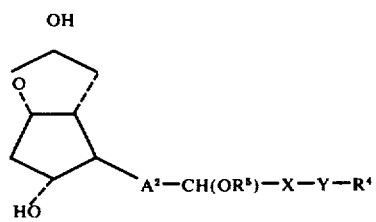

wherein $A^2$, X, Y, $R^4$ and $R^5$ have the meanings stated above, with a (4-carboxybutyl)triphenylphosphonium salt, bearing 0 or 1 alkyl substituent of 1 to 4 carbon atoms on carbon atom 2, 3 or 4, in the presence of a strong base, for example butyl-lithium or methanesulphinylmethyl sodium, whereafter when a salt is required the product is reacted with a base; or c. for those compounds wherein $R^2$ is a hydroxy radical, and $R^5$ is a hydrogen atom, the reduction of an enone of the formula:

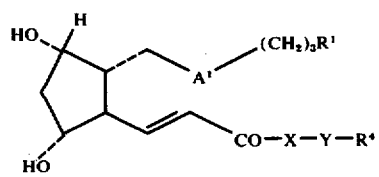

Wherein $A^1$, $R^1$, $R^4$, X and Y have the meanings stated above, and bearing 0 or 1 alkyl substituent of 1 to 4 carbon atoms on carbon atom 2, 3 or 4, with, for example, zinc borohydride, aluminium tri-isopropoxide or di-isobornyloxy aluminium isopropoxide to give a prostanoic acid derivative of the formula I wherein $A^2$ is a trans-vinylene radical, or with, for example, sodium borohydride to give a prostanoic acid derivative of the formula I wherein $A^2$ is an ethylene radical; or d. for those compounds wherein $R^1$ is an alkoxycarbonyl radical, the reaction of a compound of the formula II wherein $A^1$, $A^2$, $R^4$, $R^6$, $R^7$, X and Y have the meanings stated above, $R^8$ is a hydroxy radical and $R^3$ is a hydrogen atom, or $R^8$ and $R^3$ together form an oxo radical, and bearing 0 or 1 alkyl substituent of 1 to 4 carbon atoms on carbon atom 2, 3 or 4, with an alkanol of 1 to 10 carbon atoms in the presence of a strong acid, for example toluene-p-sulphonic acid, whereafter when a prostanoic acid derivative wherein $R^1$ is a carboxy radical is required, the ester so obtained is hydrolysed, for example with potassium hydroxide or potassium carbonate; or e. for those compounds wherein $R^1$ is an alkoxycarbonyl radical, the reaction of an acid of the formula I wherein $R^1$ is a carboxy radical with a diazoalkane of 1 to 10 carbon atoms, or of a salt thereof, for example the sodium or silver salt, with an alkyl halide of 1 to 10 carbon atoms, for example an alkyl bromide or alkyl iodide; or f. for those compounds wherein $R^1$ is a hydroxymethyl radical and Y is oxygen, sulphur or imino, or an alkylimino radical, the reduction of an ester of the formula I wherein $R^1$ is an alkoxycarbonyl radical, for example an alkoxycarbonyl radical of 1 to 11 carbon atoms, for example with a complex metal hydride, for example lithium aluminium hydride; or g. for those compounds which are 1,9α-lactones, heating a compound of the formula I wherein $R^1$ is a carboxy radical or an alkoxycarbonyl radical of 2 to 11 carbon atoms and $R^2$ is a hydroxy radical, and $A^1$, $A^2$, $R^3$, $R^4$, $R^5$, X and Y have the meanings stated above, to a temperature of about 180° C. under reduced pressure of less than $10^{-3}$mm. of mercury; or h. for those compounds which are 1,9α-lactones, the intramolecular condensation of a reactive derivative of a carboxylic acid as defined in (g) above; or i. For those compounds wherein $A^1$ is a trans-vinylene radical, the separation of a mixture of the compound of the formula I wherein $A^1$ is a cis-vinylene radical and the compound of the formula I wherein $A^1$ is a trans-vinylene radical; or j. for those compounds wherein $R^5$ is an alkyl radical, the reaction of a compound of the formula I wherein $R^5$ is a hydrogen atom with an alkyl halide, for example an alkyl iodide, in the presence of a strong base, for example sodium hydride; or k. for those compounds wherein Y is sulphinyl or sulphonyl, the oxidation of a thio-compound of the formula:

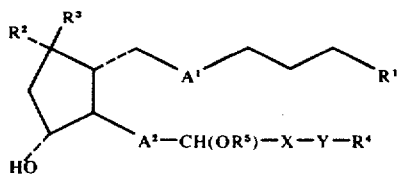

wherein $R^1$, $R^2$, $R^3$, $R^4$, $R^5$, $A^1$, $A^2$, and X have the meanings defined above, for example with sodium periodate; or l. for those compounds wherein $R^2$ is a hydroxy radical and $R^3$ is a hydrogen atom, the reduction of a compound of the invention of the formula I wherein $R^2$ and $R^3$ together form the oxo radical, and $R^1$, $R^4$, $R^5$, $A^1$, $A^2$, X and Y have the meanings stated above, for example with a complex metal hydride, for example a lithium tri(lower alkyl) hydride, such as lithium tri-s-butyl hydride, or a borohydride, for example sodium borohydride.

In process (a) a suitable mixed anhydride is a mixed anhydride with a lower alkanoic acid, for example a lower alkanoic acid of up to 8 carbon atoms, for example acetic acid, and a suitable phosphonium salt is, for example, the bromide.

The hydrolysis in process (a) may be carried out under either acidic or basic conditions, for example in aqueous acetic acid, or in an aqueous or alcoholic solution of an alkali metal carbonate, for example potassium carbonate in methanol, and it may be carried out at ambient temperature or at an elevated temperature of up to 60° C.

In process (b), the use of methanesulphinylmethyl sodium as the strong base, in a solvent such as dimethylsulphoxide, gives almost exclusively 5-cis compounds, whereas the use of n-butyl-lithium as the strong base, in a solvent such as sulpholane, gives a mixture of 5-cis and 5-trans compounds, which may be separated by process (i).

In process (h), a suitable reactive derivative of a carboxylic acid is, for example, an acid chloride; an acid anhydride; a mixed anhydride with, for example, an alkanoic acid, an arene-carboxylic acid, for example 4-phenylbenzoic acid, or a hydrogen carbonate, for example isobutyl hydrogen carbonate; or a reactive ester, for example a phenyl ester, for example a p-nitrophenyl or 2,4,5-trichlorophenyl ester. Other suitable reactive derivatives of a carboxylic acid may be obtained by reaction of the acid with a condensing agent, for example N, N'-dicyclohexylcarbodi-imide in pyridine, or N,N'-carbonyldi-imidazole in tetrahydrofuran at about 60° C.

In process (i), the separation of the mixture of cis and trans isomers may be carried out in conventional manner, for example by chromatography, for example by thin layer chromatography on silica gel impregnated with silver nitrate, or by fractional crystallisation.

The starting material of the formula III, wherein $A^2$ is the trans-vinylene radical, $R^5$ is the hydrogen atom, Y is other than sulphinyl or sulphonyl and X and $R^4$ are as defined above used in the process of the invention, may be obtained by reacting an aldehyde VI with a phosphonate $(CH_3O)_2PO.CH_2CO.XYR^4$ or a phosphorane $Ph_3P{:}CH.XYR^4$ in the presence of a strong base to give an enone VII, which is reduced to an enol VIII and hydrolysed to a diol IX. The lactone ring is then reduced with di-isobutyl aluminium hydride to give the required lactol starting material (III, $R^5$=H).

The starting material of the formula III wherein $A^2$ is an ethylene radical and Y is other than sulphinyl or sulphonyl used in the process of the invention, may be obtained by hydrogenating an enone VII, in the presence of 5% palladium-on-carbon catalyst, to give a saturated ketone, and repeating the procedure outlined above using the saturated ketone in place of an enone VII.

The starting material of the formula III wherein $R^5$ is an alkyl radical may be obtained by alkylation of the corresponding compound of the formula III wherein $R^5$ is hydrogen, for example by reaction with an alkyl halide, for example an alkyl iodide, in a solvent such as 1,2-dimethoxyethane, in the presence of a strong base such as sodium hydride.

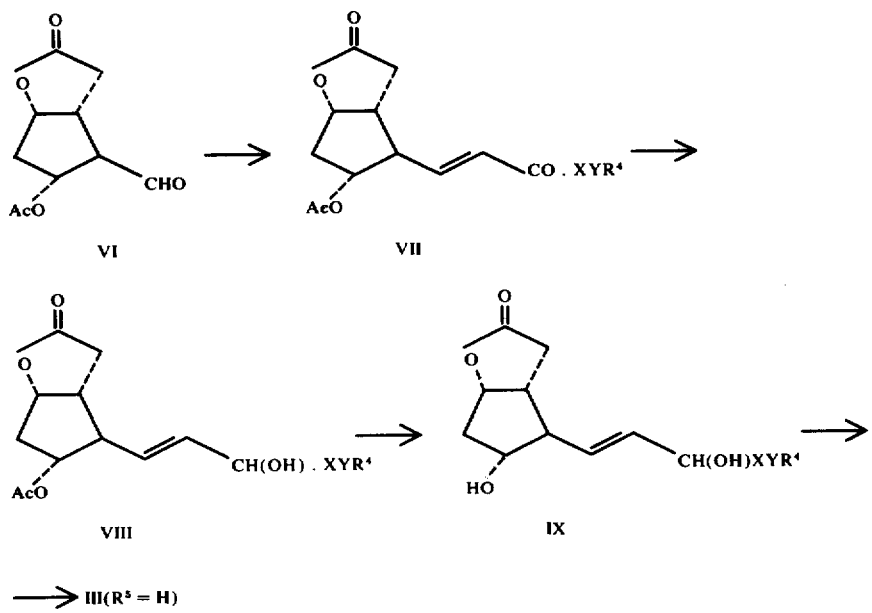

→ III(R⁵ = H)

Ac represents an acyl radical.

The starting material of the formula IV wherein $A^1$ is the cis-vinylene radical, Y is other than sulphinyl or sulphonyl and $R^1$, $R^4$ and X have the meanings stated above, used in the process of the invention, may be obtained as follows:

4β-Dimethoxymethyl-2,3,3aβ,6aβ-tetrahydro-5α-hydroxy-6β-iodo-2-oxocyclopenteno[b]furan (X) is treated with tributyl tin hydride to give the de-iodinated lactone XI. The 5α-hydroxy group is protected as the tetrahydropyran-2-yl ether XII, the lactone is reduced to the lactol XIII, using di-isobutyl aluminium hydride, and the lactol is reacted with (4-carboxy-butyl)triphenylphosphonium bromide to give the cyclopentanol derivative XIV, which by reaction with diazomethane gives the methyl ester XV. If a starting material of the formula II wherein $A^1$ is the ethylene radical is required, the methyl ester XV is hydrogenated, and the hydrogenated methyl ester is used instead of the methyl ester XV in the following steps of the process. The methyl ester is selectively hydrolysed to remove the tetrahydropyranyl and dimethyl acetal groupings, resulting in an aldehyde XVI, which is reacted with a phosphonate $(CH_3O)_2PO.CH_2CO.XYR^4$ or a phosphorane $Ph_3P{:}CH.CO.XYR^4$ in the presence of a strong base, to give the required starting material of the formula IV, wherein $A^1$ is ethylene or cis-vinylene.

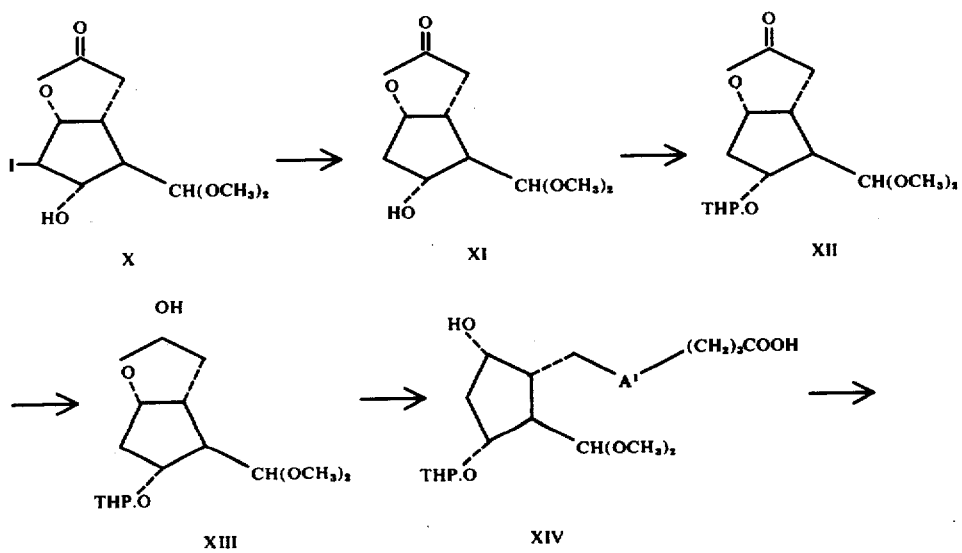

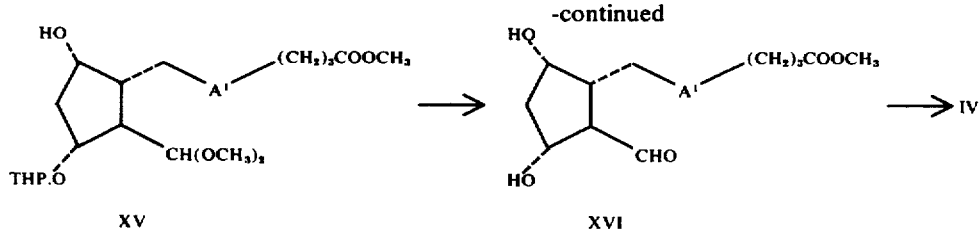

The starting material of the formula II wherein $R^8$ is hydroxy, $R^6$ and $R^7$ are both tetrahydropyranyl radicals and Y is other than sulphinyl or sulphonyl, used in the process of the invention, may be prepared by reaction of the known aldehyde XVII (Ac = acetyl or 4-phenyl- benzoyl) with a phosphonate of the formula $(CH_3O)_2.PO.CH_2CO.XYR^4$ or a phosphorane of the formula $Ph_3P:CH.CO.XYR^4$ to give an enone XVIII. The enone XVIII is reduced with zinc borohydride, aluminium tri-isopropoxide or di-isobornyloxy aluminium isopropoxide to the corresponding enol XIX, and the protecting acyl group is hydrolysed with potassium carbonate in methanol to the diol XX. The diol XX is protected as the bis-(tetrahydropyranyl ether) XXI, and the lactone ring is reduced with di-isobutyl aluminium hydride to the lactol XXII, which is reacted with a (4-carboxybutyl)triphenylphosphonium bromide in the presence of a strong base, to give the required starting material II.

The starting material of the formula II wherein $A^2$ is an ethylene radical, and Y is other than sulphinyl or sulphonyl, used in the process of the invention, may be obtained by hydrogenating an enone XVIII in the presence of 5% palladium-on-carbon catalyst, or with nickel boride, to give a saturated ketone, and repeating the procedure outlined above using the saturated ketone in place of the enone XVIII.

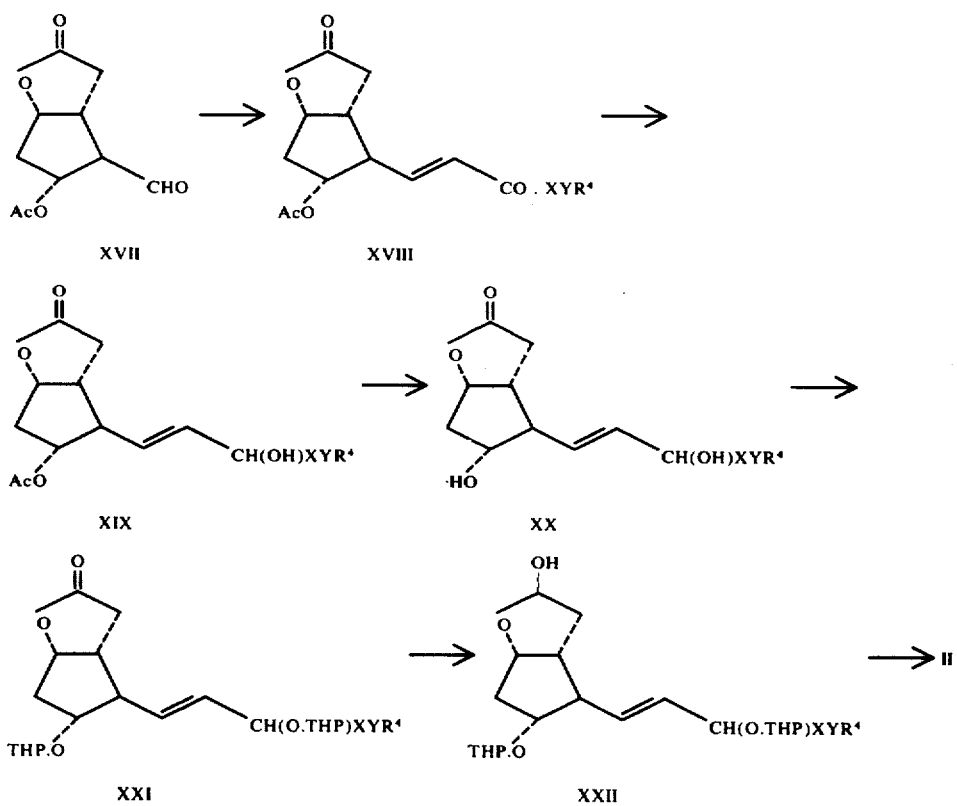

Ac represents acetyl or 4-phenylbenzoyl.

The starting material of the formula II wherein $R^2$ is an alkanoyloxy radical may be obtained from the corresponding compound wherein $R^2$ is a hydroxy radical by acylation with an acid anhydride in pyridine to give a 9-ester-1-mixed anhydride.

The starting material of the formula II wherein $R^8$ and $R^3$ together form the oxo radical, may be obtained from the corresponding starting material of the formula II, wherein $R^2$ is hydroxy and $R^3$ is hydrogen, by oxidation with Jones' reagent (chromic acid in acetone) or Collins' reagent.

The starting material of the formula II wherein $A^1$ is the cis-vinylene radical, $A^2$ is the trans-vinylene radical, $R^8$ is an acyloxy radical and $R^7$ is a hydroxy radical, may be prepared from the cyclopentanol derivative XV, by reaction with an acylating agent, for example 4-phenylbenzoyl chloride, to give the phenylbenzoate ester XXIII which is selectively hydrolysed to remove the tetrahydropyranyl and dimethyl acetal groupings, resulting in an aldehyde XXIV. The aldehyde XXIV is reacted with a phosphonate or phosphorane as described above to give an enone XXV which, on reduction with zinc borohydride, aluminium tri-isopropoxide or di-isobornyloxy aluminium isopropoxide gives the required starting material II.

The corresponding starting material of the formula II wherein $A^1$ is the ethylene radical may be prepared similarly from the ester obtained by hydrogenation of the phenylbenzoate ester XXIII, and the corresponding starting material of the formula I wherein $A^2$ is the ethylene radical may be prepared by using sodium borohydride for the reduction of the enone XVIII.

and $R^7$ and $R^8$ are each an acyloxy radical, may be prepared from the methyl ester XV by selective hydrolysis of the tetrahydropyranyl radical, for example by toluene-p-sulphonic acid in tetrahydrofuran, to a diol XXVI, which is reacted with an acylating agent, for example 4-phenylbenzoyl phenylbenzoyl chloride, to give a bis-phenylbenzoate ester XXVII which is hydrolysed to the corresponding aldehyde XXVIII. The aldehyde XXVIII is reacted with a phosphonate or phosphorane as described above to give an enone XXIX which is reduced as described above to the required starting material II.

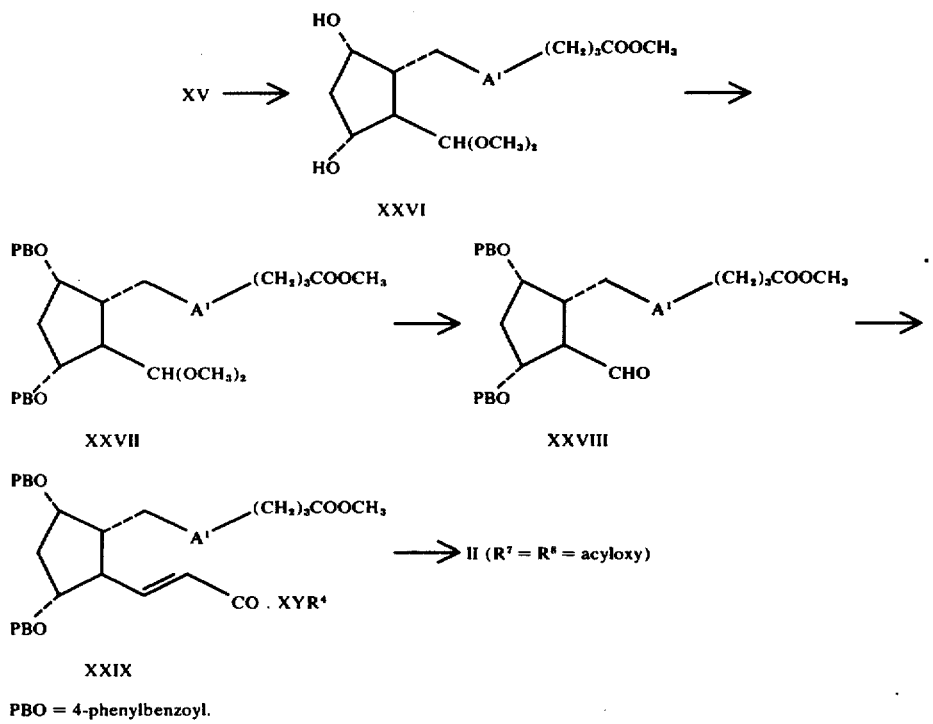

The corresponding starting materials of the formula

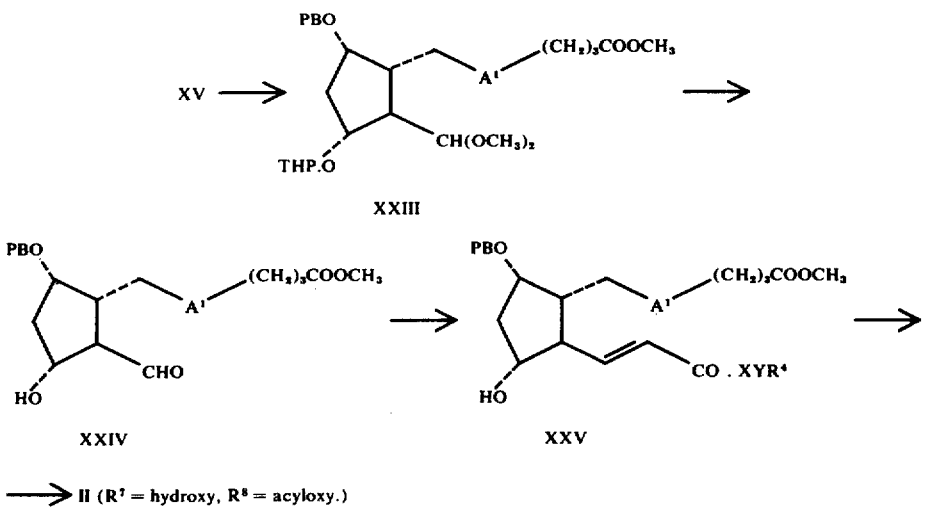

The starting material of the formula II wherein $A^1$ is the cis-vinylene radical, $A^2$ is the trans-vinylene radical II wherein either or both of $A^1$ and $A^2$ is an ethylene radical may be prepared in a similar manner to that described above for the case where $R^7$ is a hydroxy radical and $R^8$ is an acyloxy radical.

It is, of course, to be understood that an optically active compound of the invention may be obtained either by resolving the corresponding racemate, or by carrying out the above-described reaction sequences starting from an optically active intermediate, for example from an optically active aldehyde of the formula XVII (Ac = acetyl or p-phenylbenzoyl).

As stated above, the compounds of the invention possess a profile of pharmacological properties which differs from that of the naturally occurring prostaglandins $F_2\alpha$ and $E_2$. Thus, for example either C-15 epimer of 9α,11α,15-trihydroxy-16-(indol-5-yloxy)-17,18,19,20-tetranor-5-cis, 13-trans-prostadienoic acid is at least 100 times as active as prostaglandin $F_2\alpha$ as a luteolytic agent, yet has only less than one twenty fifth of the smooth muscle stimulant activity of prostaglandin $F_2\alpha$.

When a compound of the invention is to be used, for example for the induction of labour, it is used in the same way as it is known to use the naturally-occurring prostaglandins $E_2$ and $F_2\alpha$, that is to say, by administering a sterile, substantially aqueous solution containing up to 1mg./ml. of active compound, by intravenous infusion, by transcervical extra-amniotic infusion or intra-amniotic infusion, until labour commences.

Thus, according to a further feature of the invention there is provided a pharmaceutical or veterinary composition comprising a prostanoic acid derivative of the formula 1 together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for infusion, for example sterile aqueous or oily solutions or suspensions, or in the form of a suppository, suitable for anal or vaginal use.

The compositions of the invention may be prepared by conventional means, and may incorporate conventional excipients.

The invention is illustrated but not limited by the following Examples. Throughout the Examples $R_F$ values refer to silica gel plates supplied commercially by Merck of Darmstadt, and the spots were detected either by fluorescence under unltra-violet radiation, or by spraying the plates with a solution of ceric ammonium nitrate in sulphuric acid. Mass spectrum data refer to the pertrimethylsilyl derivatives, that is, normally, tetra-trimethylsilyl derivatives of compounds wherein $R^1$ is carboxy or hydroxymethyl, and tri-trimethylsilyl derivatives of compounds wherein $R^1$ is an alkoxycarbonyl radical.

EXAMPLE 1

Finely powdered (4-carboxybutyl)triphenyl phosphonium bromide (0.346g.) was heated to 100° C. under vacuum for 1 hour. The evacuated reaction vessel was filled with an atmosphere of dry nitrogen, the solid was dissolved in dimethylsulphoxide (1ml.) and the solution was cooled to room temperature. To this solution was added dropwise 0.71ml. of a 2M solution of methanesulphinylmethyl sodium in dimethyl sulphoxide followed by a solution of a mixture of epimers of 2,3,3aβ,6aβ-tetrahydro-2,5α-dihydroxy-4β-[3-hydroxy-4-(pyrid-3-yloxy)-1-trans-butenyl]cyclopenteno[b]furan (40mg.) in a mixture of dimethylsulphoxide (1ml.) and toluene (0.2ml.). The solution was stirred for 2 hours, and the solvent was removed by evaporation under reduced pressure at a temperature below 40° C. The residue was shaken with saturated brine (2ml.) and extracted with ether (3 × 2ml.), and the extracts were discarded. The aqueous solution was adjusted to pH 5 with saturated oxalic acid, and extracted with ethyl acetate (6 × 2ml.). Evaporation of the solvent gave a crude product which was further purified by dissolving in chloroform (2ml.) and extracting with N hydrochloric acid (3 × 0.5ml.). The combined extracts were neutralised to pH 7 with saturated aqueous sodium carbonate solution, and the water was removed by azeotropic distillation with toluene, and extraction with acetone gave sodium 9α,11α,15-trihydroxy-16-(pyrid-3-yloxy)-17,18,19,20-tetranor-5-cis, 13-trans-prostadienoate, as mixed C-15 epimers. Acidification gave the free acid as mixed C-15 epimers, $R_F$ = 0.2 (20% methanol in ethyl acetate). The n.m.r. spectrum of the free acid in deuterated methanol showed the following characteristic peaks (δ values):

8.1, 2H, aromatic protons
7.4, 2H, aromatic protons
5.37–5.7, 4H, olefinic protons The mass spectrum showed $M^+ = 679.3577$ (calculated for $C_{33}H_{61}NO_6Si_4 = 679.3615$).

The lactol used as starting material may be prepared as follows:

n-Butyl-lithium (4.76ml. of a 2.1M solution in hexane) was added to a solution of dimethyl methylphosphonate (1.24g.) in dry tetrahydrofuran at −78° C. in an atmosphere of nitrogen. After 10 minutes, a solution of ethyl 3-pyridyloxyacetate (0.90g.) in dry tetrahydrofuran (5ml.) was added dropwise, and the mixture was stirred for 1 hour at −78° C. The reaction mixture was taken to pH 1-2 with 2N hydrochloric acid and the solvents were removed under reduced pressure. The residue was shaken with water (10ml.) and extracted with ether (3 × 10ml.). The extracts were discarded, and the aqueous solution was adjusted to pH 7-8 with sodium bicarbonate solution and extracted with chloroform (6 × 10ml.). The combined extracts were evaporated, to give dimethyl [2-oxo-3-(pyrid-3-yloxy)-propyl]phosphonate as an oil, $R_F = 0.2$ (10% methanol in ethyl acetate).

A solution of the phosphonate (1.17g.) in dry 1,2-dimethoxyethane (20ml.) at 0° C. was treated with sodium hydride (0.187g. of a 50% dispersion in oil) and the mixture was stirred for 25 minutes. To this mixture was added 4β-formyl-2,3,3aβ,6aβ-tetrahydro-2-oxo-5α-(4-phenylbenzoyloxy)-cyclopenteno[b]furan (1.05g.) and after 1 hour the reaction mixture was neutralised with glacial acetic acid and all solvents were removed by evaporation under reduced pressure below 35° C. The residue was dissolved in ethyl acetate (20ml.) and extracted with N hydrochloric acid (3 × 5ml.). The combined extracts were neutralised with sodium carbonate solution and extracted with ethyl acetate, and the extracts were dried and evaporated to give the enone, 2,3,3aβ,6aβ-tetrahydro-2-oxo-4β-[3-oxo-4-(pyrid-3-yloxy)-1-trans-butenyl]-5α-(4-phenylbenzoyloxy)-cyclopenteno[b]furan m.p. 143°–148° C., $R_F = 0.3$ (ethyl acetate).

To a solution of the enone (500mg.) in dry toluene (20ml.) was added 15ml. of a 0.3M solution of di-isobornyloxy-aluminium isopropoxide in toluene. The mixture was stirred at room temperature for 2½ hours, then saturated sodium hydrogen tartrate solution was added until effervescence ceased. Ethyl acetate (100ml.) was added, the organic layer was separated, washed with a 1:1 mixture of saturated brine and water, then dried. The solvents were evaporated to give a mixture of epimeric enols, 2,3,3a$\beta$,6a$\beta$-tetrahydro-4$\beta$-[3-hydroxy-4-(pyrid-3-yloxy)-1-trans-butenyl]-2-oxo-5$\alpha$-[4-phenylbenzoyloxy]cyclopenteno[b]furan, $R_F$ = 0.4 (10% methanol in ethyl acetate).

The mixture of epimeric enols (500mg.) was stirred vigorously for 2 hours with finely powdered anhydrous potassium carbonate (150mg.) in methanol (10ml.). The solution was neutralised with N hydrochloric acid, and the solvent was evaporated under reduced pressure. The residue was made acid by addition of N hydrochloric acid (5ml.), and extracted with ether (3 × 2ml.). The extracts were discarded, and the aqueous layer was neutralised with 10% sodium carbonate solution and extracted with chloroform (6 × 10ml.). The extracts were combined and dried, and the solvent was evaporated to give a mixture of epimeric diols, 2,3,3a$\beta$,6a$\beta$-tetrahydro-5$\alpha$-hydroxy-4$\beta$-[3-hydroxy-4-(pyrid-3-yloxy)-1-trans-butenyl]-2-oxocyclopenteno[b]furan, $R_F$ = 0.2 (10% methanol in ethyl acetate).

To a solution of the epimeric diols (60mg.) in a mixture of dry toluene (2ml.) and dimethoxyethane (2ml.) under an atmosphere of nitrogen at −78° C. was added 1ml. of a 1.7 m. mole/ml. solution of di-isobutyl aluminium hydride in toluene. After 15 minutes the reaction was quenched by the dropwise addition of methanol (3ml.) and after a further 15 minutes at room temperature the mixture was extracted with ethyl acetate (6 × 10ml.). The extract was washed with saturated brine (2ml.), and dried, and the solvents were evaporated to give a mixture of epimers of 2,3,3a$\beta$,6a$\beta$-tetrahydro-2,5$\alpha$-dihydroxy-4$\beta$-[3-hydroxy-4-(pyrid-3-yloxy)-1-trans-butenyl]cyclopenteno[b]furan.

EXAMPLE 2

A solution of 9$\alpha$-hydroxy-17-(4-pyridyl)-11$\alpha$,15-bis(tetrahydropyran-2-yloxy)-18,19,20-trinor-5-cis,13-trans-prostadienoic acid (147mg.) in 9.5ml. of a mixture of acetic acid (5ml.), water (5ml.) and tetrahydrofuran (3ml.) was stirred at 50° C. for 2½ hours., and the solvents were then evaporated to leave a residue consisting of the mixed C-15 epimers of 9$\alpha$,11$\alpha$,15-trihydroxy-17-(4-pyridyl)-18,19,20-trinor-5-cis,13-trans-prostadienoic acid and polymerised dihydropyran. The mixture of C-15 epimers was separated from polymeric material by thin layer chromatography, developing with 20% methanol in methylene dichloride, $R_F$ = 0.55; mass spectrum $M^+$ = 677.3794 (calculated for $C_{34}H_{63}NO_5Si_4$ = 677.3785).

the bis(tetrahydropyranyl ether) used as the starting material in the above process may be obtained as follows:

The process described in Example 1 for the preparation of dimethyl [2-oxo-3-(pyrid-3-yloxy)propyl]-phosphonate was repeated, using ethyl 3-(pyrid-4-yl)propionate in place of ethyl 3-pyridyloxyacetate, to give dimethyl [2-oxo-4-(pyrid-4-yl)butyl]phosphonate, $R_F$ = 0.63 (acetone). The n.m.r. spectrum in deuteriochloroform showed the following characteristic absorptions ($\delta$ values):

| 2.40–2.50, | 4H, | multiplet, | —CH$_2$.CH$_2$— |
| 5.86–6.00, | 2H, | multiplet, | pyridine protons. |
| 7.00–7.13, | 2H, | multiplet, | |

A solution of dimethyl [2-oxo-4-(pyrid-4-yl)butyl]-phosphonate (1.49g.) in dry 1,2-dimethoxyethane (40ml.) was cooled to −78° C., and treated with n-butyl-lithium (2.52ml. of a 2.1M solution in hexane), and the mixture was stirred for 5 minutes. Solid 4$\beta$-formyl-2,3,3a$\beta$,6a$\beta$-tetrahydro-2-oxo-5$\alpha$-(4-phenylbenzoyloxy)cyclopenteno[b]furan (1.7g.) was added, the mixture was kept at room temperature for 1¼ hours, and neutralised with glacial acetic acid, and all solvents were then removed by evaporation under reduced pressure below 35° C. The residue was partitioned between ethyl acetate and water, the ethyl acetate layer was separated and dried, and the solvents were evaporated. The residue was solidified by trituration with ether, and the solid was filtered off and dried, to give the enone 2,3,3a$\beta$,6a$\beta$-tetrahydro-2-oxo-4$\beta$-[3-oxo-5-(pyrid-4-yl)pent-1-trans-enyl]-5$\alpha$-(4-phenylbenzoyloxy)cyclopenteno[b]furan as a white solid, $R_F$ = 0.53 (acetone).

The enone was reduced to the corresponding enol, and the enol hydrolysed to the corresponding diol, by the process described in Example 1.

To a solution of the epimeric diols (506mg.) in methylene dichloride (13ml.) under an atmosphere of nitrogen were added successively redistilled 2,3-dihydropyran (0.98ml.) and anhydrous toluene-p-sulphonic acid (318mg., 1 equivalent), followed by a solution of toluene-p-sulphonic acid (0.2ml. of a 0.1M solution). After 10 minutes, a few drops of pyridine were added, and the solution was washed successively with saturated sodium bicarbonate solution and saturated brine, and was dried. Evaporation of the solvents gave a mixture of epimeric bis(tetrahydropyranyl ethers), 2,3,3a$\beta$,6a$\beta$-tetrahydro-2-oxo-4$\beta$-[5-(pyrid-4-yl)-3-(tetrahydropyran-2-yloxy)pent-1-trans-enyl]-5$\alpha$-(tetrahydropyran-2-yloxy)cyclopenteno[b]furan, as a clear oil, $R_F$ = 0.5 (acetone), which was purified by chromatography on a silica column ("Florisil" — trade mark), eluting successively with ether, ethyl acetate and 10% methanol in toluene.

To a solution of the epimeric bis(tetrahydropyranyl ethers), (390mg.) in dry toluene (8ml.) under an atmosphere of nitrogen at −78° C. was added 1.5ml. of a 1.72 m.mole/ml. solution of di-isobutyl aluminium hydride in toluene. The course of the reaction was monitored by thin layer chromatography, and when the reaction was complete, methanol (3.5ml.) was added. The mixture was kept at room temperature for 15 minutes, ethyl acetate (30ml.) and brine (10ml.) were added, the mixture was filtered and the ethyl acetate layer was separated and dried. The solvent was evaporated, and the residue consisted of the mixed epimers of 2,3,3a$\beta$,6a$\beta$-tetrahydro-2-hydroxy-4$\beta$-[5-(pyrid-4-yl)-3-(tetrahydropyran-2-yloxy)-pent-1-trans-enyl]-5$\alpha$-(tetrahydropyran-2-yloxy)cyclopenteno[b]furan, $R_F$ = 0.06 (20% methanol in toluene).

Finely powdered (4-carboxybutyl)triphenylphosphonium bromide (674mg.) was heated to 60° C. under vacuum for 1 hour. The evacuated reaction vessel was filled with an atmosphere of dry nitrogen, the solid was dissolved in dimethylsulphoxide (0.7ml.) and the solution was cooled to room temperature. To this solution was added dropwise 1.44ml. of a 2M solution of methanesulphinylmethyl sodium in dimethyl sulphoxide followed by benzene (0.45ml.). A solution of the mixture of epimers of the cyclopenteno[b]furan bis-(tetrahydropyranyl ether) (271mg.) in dimethylsulphoxide (3.75ml.) was added, the mixture was stirred for 45 minutes, a few drops of water were added, and the solvent was removed by evaporation under reduced pressure at a temperature below 40° C. The residue was shaken with water (30ml.) and ether (20ml.), and the aqueous phase was separated, extracted with more ether (3 × 20ml.) and the extracts discarded. The aqueous solution was acidified to pH 5 with 2N aqueous oxalic acid, extracted with a mixture of equal parts of ether and petroleum ether (b.p. 40°–60° C.) (5 × 15ml.), and the combined organic extracts were dried. Evaporation of the solvents gave 9α-hydroxy-17-(pyrid-4-yl)-11α,15-bis-(tetrahydropyran-2-yloxy)-18,19,20-trinor-5-cis, 13-trans-prostadienoic acid as a clear oil, $R_F = 0.68$ (20% methanol in methylene dichloride).

EXAMPLE 3

The process described in Example 2 was repeated, using the corresponding 16-(4,6-dimethyl-2-pyridyloxy) bis-(tetrahydropyranyl ether) in place of the 17-(4-pyridyl) compound, to give the mixed C-15 epimers of 16-(4,6-dimethylpyrid-2-yloxy)-9α,11α,15-trihydroxy-17,18,19,20-tetranor-5-cis, 13-trans-prostadienoic acid. The mass spectrum showed $M^+ = 707.3925$ (calculated for $C_{35}H_{65}NO_6Si_4 = 707.3980$).

The bis(tetrahydropyranyl ether) starting material was prepared by the sequence of processes described in the second part of Example 2, starting from ethyl 3-(4,6-dimethylpyrid-2-yloxy)acetate instead of ethyl 3-(pyrid-4-yl)propionate, via the phosphonate, dimethyl [2-oxo-3-(4,6-dimethylpyrid-2-yloxy)propyl]phosphonate, $R_F = 0.7$ (10% methanol in ethyl acetate), and the corresponding enone, 4β-[4-(4,6-dimethylpyrid-2-yloxy)-3-oxobut-1-trans-enyl]-2,3,3aβ,6aβ-tetrahydro-2-oxo-5α-(4-phenylbenzoyloxy)cyclopenteno[b]furan, m.p. 130°–135+ C.

EXAMPLE 4

Methyl 15-hydroxy-16-(indole-5-yloxy)-9α,11α-di-(4-phenylbenzoyloxy)-17,18,19,20-tetranor-5-cis, 13-trans-prostadienoate (128mg.) was stirred at room temperature under argon in a mixture of methanol (15ml.), water (5ml.) and 1,2-dimethoxyethane (15ml.) with potassium hydroxide (400mg.) for 16 hours. Glacial acetic acid was added to adjust the pH of the solution to 6, and the solvents were evaporated under reduced pressure. The residue was partitioned between water and ethyl acetate, and the aqueous layer was acidified to pH 3–4 with 2N oxalic acid. The aqueous layer was separated and washed with ethyl acetate, the combined ethyl acetate solutions were washed with brine and dried, and the solvent was evaporated to leave a solid residue of 4-phenylbenzoic acid and the mixed C-15 epimers of 9α,11α,15-trihydroxy-16-(indol-5-yloxy)-17,18,19,20-tetranor-5-cis, 13-trans-prostadienoic acid. The mixed epimers were separated by thin layer chromatography, using 3% acetic acid in ethyl acetate, $R_F = 0.3$ and 0.45. The n.m.r. spectrum, in deuterated acetone, of either epimer showed the following characteristic absorptions ( δ values):

6.7–7.4, 4H, aromatic protons 6.35, 1H, proton at indole C-3

The mass spectrum of the more polar epimer showed $M^+ = 717.3662$ (calculated for $C_{36}H_{63}NO_6Si_4 = 717.3734$).

The methyl ester used as starting material in the above process may be prepared as follows:

Sodium hydride (1.4g. of 57% dispersion in oil) was washed free of oil with dry pentane then suspended in dry 1,2-dimethoxyethane (8ml.) under an atmosphere of argon. The mixture was cooled in an ice bath and a solution of 5-hydroxyindole (4.00g.) in dry 1,2-dimethoxyethane (24ml.) was added slowly. The ice bath was removed and stirring was continued for 10 minutes. A solution of ethyl bromoacetate (3.33ml.) in dry 1,2-dimethoxyethane (24ml.) was added slowly, stirring was continued for 2 hours, then the mixture was filtered and the filtrate was evaporated to dryness. The residue was partitioned between ether and 1N sodium hydroxide solution, the ether layer was separated, washed with water and dried, and the solvent was evaporated to give ethyl 5-indolyloxyacetate, m.p. 74° –77° C.

n-Butyl-lithium (21.8ml. of a 2.29M solution in hexane) was added to a solution of dimethyl methylphosphonate (6.2g.) in dry tetrahydrofuran (50ml.) at −78° C. in an atmosphere of argon. After 10 minutes, a solution of ethyl 5-indolyloxyacetate (5.5g.) in dry tetrahydrofuran (50ml.) was added dropwise, and the mixture was stirred for 2 hours at −78° C. The reaction mixture was poured into 2N hydrochloric acid and stirred vigorously for 5 minutes, then the solvents were evaporated under reduced pressure. The residue was shaken with a mixture of ethyl acetate and water, and the organic phase was separated and washed with brine. The solution was dried, the solvents were evaporated and the residue was chromatographed on a column of silica gel MFC (250g.) using methylene dichloride : ethyl acetate mixtures as eluant, to give dimethyl [2-oxo-3-(indol-5-yloxy)propyl]phosphonate as an oil, $R_F = 0.3$ (ethyl acetate).

A solution of dimethyl [2-oxo-3-(indol-5-yloxy)propyl]phosphonate (138mg., 1.5 equivalent) in 1,2-dimethoxyethane (3ml.) was stirred under argon and cooled in an acetone/'Drikold' bath, and treated with 2.29M n-butyl-lithium in hexane (176μl.) followed after a few minutes by a solution of methyl 7-[2β-formyl-3α,5α-di-(4-phenylbenzoyloxy)cyclopent-1α-yl]hept-5-cis-enoate (195mg.), also in 1,2-dimethoxyethane (4ml.). After 2 hours, the cooling bath was removed and the mixture was stirred overnight at ambient temperature. A few drops of acetic acid and then water (200μl.) were added to adjust the pH to about 6. The solvent was evaporated under reduced pressure and the residue was partitioned between water and ethyl acetate. The organic layer was separated, washed with water (10ml.) then dried over magnesium sulphate and filtered, and the solvent was evaporated to give a viscous oil. This oil was purified by thin layer chromatography eluting twice with ether, to afford the enone, methyl 16-(indol-5-yloxy)-15-oxo-9α,11α-di-(4-phenyl-benzoyloxy)-17,18,19,20-tetranor-5-cis, 13-trans-prostadienoate, $R_F = 0.37$ (15% ethyl acetate in toluene). The n.m.r. spectrum in deuteriochloroform showed the following characteristic absorptions ( δ values):

3.53, 3H, singlet, —CO₂CH₃

4.72, 2H, singlet, —CO.CH₂O—

5.2–5.6, 4H, multiplet, cis-olefinic protons, >CH.OCO—

6.4, 1H, indole C-3 protons 6.68, 1H, doublet (J = 16 Hz), —CH=CH.CO—

The enone (150mg.) was stirred in dry toluene (5.0ml.) under argon at room temperature, and treated with a 0.323M solution of di-isobornyloxyaluminium isoproxide in toluene (1.16ml., 2 equivalents). After 5 hours, the mixture was partitioned between water and ethyl acetate and filtered through kieselguhr ("Hyflo"- trade mark), washing the filter pad with ethyl acetate. The organic layer was separated, washed with brine, dried over magnesium sulphate and filtered, and the solvent was evaporated to leave a crude product, which was purified by thin layer chromatography using 10% ethyl acetate in toluene as the eluant. The enol, methyl 15-hydroxy-16-(indol -5-yloxy)-9α,11α-di-(4-phenylbenzoyloxy)-17,18,19,20-tetranor-5-cis, 13-trans-prostadienoate, was obtained as a viscous oil, $R_F = 0.16$ (10% ethyl acetate in toluene).

The aldehyde, methyl 7-[2β-formyl-3α,5α-di-(4-phenylbenzoyloxy)cyclopent-1α-yl]hept-5-cis-enoate, used in the above process, may be prepared as follows:

4β-Dimethoxymethyl-2,3,3aβ,6aβ-tetrahydro-5α-hydroxy-6β-iodo-2-oxocylcopenteno[b]furan (4.0g.) in dry toluene (40ml.) was stirred under argon at 80°C. with tri-n-butyl tin hydride (6.6g.) for 18 hours. The solvent was evaporated under reduced pressure and the residue was stirred with petroleum ether (b.p. 40°–60° C., 100ml.) for 30 minutes. The solvent was decanted and the residual oil was chromatographed on Florisil (trade mark) (50g.). Elution with mixtures containing 25% ethyl acetate in toluene and finally with ethyl acetate gave 4β-dimethoxymethyl-2,3,3aβ,6aβ-tetrahydro-5α-hydroxy-2-oxocyclopenteno[b]furan as an oil, $R_F = 0.3$ (20% acetone in chloroform). The n.m.r. spectrum in deuteriochloroform showed the following characteristic peaks (δ values):

| | | | |
|---|---|---|---|
| 3.40 and 3.42, | 6H, | 2 singlets, | methoxy |
| 4.04–4.36 | 1H, | multiplet, | 5β proton |
|  | 1H, | doublet, | —CH(OMe)₂ |
|  | 1H, | multiplet, | 6aβ proton |

4β-Dimethoxymethyl-2,3,3aβ,6aβ-tetrahydro-5α-hydroxy-2-oxocyclopenteno[b]furan (4.01g.) was stirred under argon in dry toluene (30ml.), and the resulting solution was treated with an excess of freshly distilled 2,3-dihydropyran (17ml.), followed by 2.0ml. of a 0.1% w/v solution of toluene-p-sulphonic acid in dry tetrahydrofuran. After three-fourths hour, the mixture was treated with pyridine (0.50ml.) and then partitioned between ethyl acetate (150ml.) and saturated sodium bicarbonate (75ml.). The organic layer was separated, washed with saturated brine (50ml.), dried over magnesium sulphate and filtered, and the solvent was evaporated to give a crude lactone, 4β-dimethoxymethyl-2,3,3aβ,6aβ-tetrahydro-2-oxo-5α-(tetrahydropyran-2-yloxy)-cyclopenteno[b]furan, $R_F = 0.70$ (20% acetone in chloroform). The crude lactone (6.2g.) was dissolved by stirring in dry 1,2-dimethoxyethane (120ml.) under argon at about −60° C. (chloroform - Drikold (trade mark) cooling bath), and 1.7M di-isobutylaluminium hydride (11.2ml.) was added. After 30 minutes, methanol (3ml.) was added, the mixture was allowed to warm up to room temperature, and was partitioned between ethyl acetate (600ml.) and 1:1 saturated brine/water (300ml.). The whole mixture was filtered through keiselguhr (Hyflo - trade mark) and the two phases were separated. The aqueous phase was re-extracted with ethyl acetate (300ml.) and the combined organic layers were washed with water (100ml.), dried over magnesium sulphate and filtered, and the solvents were evaporated to give the crude lactol, 4β-dimethoxymethyl-2,3,3aβ,6aβ-tetrahydro-2-hydroxy-5α-(tetrahydropyran-2-yloxy)cyclopenteno[b]furan, as an oil, $R_F = 0.4$ (20% acetone in chloroform).

A stirred solution of (4-carboxybutyl)triphenylphosphonium bromide (24.8g.) in dry dimethylsulphoxide (DMSO, 50ml.). was treated slowly under argon and with cooling in an ice-water bath, with 2M methanesulphinylmethyl sodium in DMSO (54.5ml., 2.5 equivalents) to form a solution of the corresponding ylide. The crude lactol (6.3g.) in dry DMSO (150ml.) was then added to the ylide solution at room temperature. The mixture was stirred for 1¼ hours, then water (1ml.) was added. The DMSO was then evaporated at high vacuum at a temperature not exceeding 50° C. The residual gum was partitioned between ether (4 × 225ml.) and water (150ml.). The aqueous layer was separated, acidified with 2N oxalic acid to approximately pH 4, and then extracted with 1:1 mixture of ether and pentane (3 × 300ml.). The extracts were washed with saturated brine (150ml.), dried over magnesium sulphate and filtered, and the solvent was evaporated to give the crude acid, 7-[2β-dimethoxymethyl-5α-hydroxy-3α-(tetrahydropyran-2-yloxy)cyclopent-1α-yl]hept-5-cis-enoic acid as an oil, suitable for use in the next stage of the synthesis. A sample was purified by chromatography on silica (70:1) eluting the product with 2% methanol in toluene as an oil $R_F = 0.4$ (5% methanol in methylene chloride). The n.m.r. spectrum in deuteriochloroform showed the following characteristic peaks (δ values):

| | | | |
|---|---|---|---|
| 3.35, | 6H, | singlet, | methoxy |
| 3.3–3.65, | 1H, | | |
| 3.68–4.0, | 1H, | | |
| 4.00–4.19, | 2H, | } multiplets, >CH—O— | |
| 4.19–4.38, | 1H, | | |
| 4.6–4.8, | 1H, | | |
| 5.09–5.78, | 2H, | multiplet, | olefinic protons |

The crude acid (4.48g.) in methanol (45ml.) was stirred under argon at room temperature with toluene-p-sulphonic acid (240mg.) for 2¾ hours. The solution was then partitioned between ethyl acetate (300ml.) and saturated sodium bicarbonate (60ml.) followed by saturated brine (60ml.). The organic phase was dried over magnesium sulphate and filtered, and the solvent was evaporated to leave a crude ester-diol, methyl 7-[2β-dimethoxymethyl-3α,5α-dihydroxy-cyclopent-1α-yl]hept-5-cis-enoate as an oil, $R_F = 0.65$ (10% methanol in methylene chloride). The n.m.r. spectrum in deuteriochloroform showed the following principal peaks (δ values):

| | | | |
|---|---|---|---|
| 3.39, | 6H, | singlet | } 3 methyl groups |
| 3.64, | 3H, | singlet | |
| 4.03–4.3, | 3H, | { multiplet, >CH—O—  doublet, >CH(OMe)₂ | |
| 5.1–5.7, | 2H, | multiplet, | olefinic protons |

The crude ester-diol (3.3g.) was dissolved in dry pyridine (50ml.) under argon, and treated with p-phenylbenzoyl chloride (9.2g.), and the mixture was stirred for 17 hours. Water (0.8ml.) was then introduced and stirring was continued for 3–4 hours. The mixture was evaporated under reduced pressure and toluene was added to assist azeotropic removal of the pyridine. The residue was partitioned between toluene (300ml.) and saturated sodium bicarbonate solution (150ml.). The whole mixture was filtered through Hyflo and the organic phase was separated. The aqueous layer was extracted with toluene (150ml.), and the organic extracts were combined, washed with brine (100ml.), dried over magnesium sulphate, and filtered, and the solvent was evaporated to leave a solid crystalline residue. This was thoroughly triturated with methanol (70ml.), the mixture was filtered, and the product was washed with more methanol (3 × 10ml.) to give the dimethyl acetal, methyl 7-[2β-dimethoxymethyl-3α,5α-di-(4-phenylbenzoyloxy)cyclopent-1α-yl]hept-5-cis-enoate as a white solid, m.p. 104.5°–106.5° C., $R_F$ = 0.5 (5% acetone in toluene). The n.m.r. spectrum in deuteriochloroform showed the following characteristic signals (δ values):

| | | | |
|---|---|---|---|
| 3.41, | 3H, | singlet | |
| 3.47, | 3H, | singlet | methyls |
| 3.52, | 3H, | singlet | |

4.59–4.61, 1H, doublet, >CH(OMe)₂

5.17–5.70, 4H, multiplet, 2 × >CH—O— and 2 olefinic protons 7.80–8.00, 2H, 8.00–8.20, 2H, } doublet, —⟨C₆H₄⟩—CO.O—

An analytical sample recrystallised three times from ethanol had m.p. 105°–107° C. The dimethyl acetal was vigorously stirred under argon for 10 minutes in a two-phase system consisting of 2% isopropanol in chloroform (20ml.) and concentrated hydrochloric acid (10ml.). The chloroform layer was separated and the aqueous layer was extracted with chloroform (20ml.). The organic layers were combined, washed successively with aqueous saturated sodium bicarbonate (20ml.) and saturated brine (10ml.), dried over magnesium sulphate and filtered, and the solvent was evaporated. The oily residue crystallised on drying under high vacuum to give methyl 7-[2β-formyl-3α,5α-di-(4-phenylbenzoyloxy)cyclopent-1α-yl]hept-5-cis-enoate, $R_F$ = 0.4 (5% ethyl acetate in toluene). The n.m.r. spectrum in deuteriochloroform was consistent with the required structure, and showed the following principal signals (δ values):

3.51, 3H, singlet, methyl ester 5.3–5.6, 4H, multiplet, >CH—O— and olefinic protons

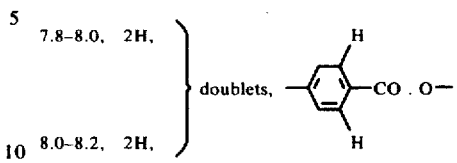

7.8–8.0, 2H, 8.0–8.2, 2H, } doublets, —⟨C₆H₄⟩—CO.O—

7.22–7.73, 14H, multiplet, rest of aromatic protons 10.01–10.14, 1H, doublet, —CHO An analytical sample, m.p. 93°–97° C., was obtained by triturating the above-described product with ether.

EXAMPLE 5

The process described in Example 4 was repeated, using the appropriate methyl ester in place of the indol-5-yloxy methyl ester, to give the following compounds:

a. 9α,11α,15-trihydroxy-16-(1-methylindol-5-yloxy)-17,18,19,20-tetranor-5-cis, 13-trans-prostadienoic acid, $R_F$ = 0.4 and 0.5 (3% acetic acid in ethyl acetate). The mass spectrum of the more polar epimer showed $M^+$ = 731.3886 (calculated for $C_{37}H_{65}NO_6Si_4$ = 731.3890).

The methyl ester starting material was prepared by the process described in the second part of Example 4, starting from 5-hydroxy-1-methylindole instead of 5-hydroxyindole, via the corresponding phosphonate, $R_F$ = 0.22 (ethyl acetate), n.m.r. in deuteriochloroform:

δ 6.35, 1H, indole C-3 proton 4.65, 2H, —CO.CH₂O— and the corresponding enone, $R_F$ = 0.42 (25% pentane in ether).

b. 16-(3-chloroindol-5-yloxy)-9α,11α,15-trihydroxy-17,18,19,20-tetranor-5-cis, 13-trans-prostadienoic acid, $R_F$ = 0.4 and 0.5 (3% acetic acid in ethyl acetate), $M^+$ (for more polar epimer) = 751.3335 (calculated for $C_{36}H_{62}ClNO_6Si_4$ = 751.3344).

The methyl ester starting material was obtained by chlorination of the 16-(indol-5-yloxy) methyl ester starting material described in Example 4 as follows:

Methyl 15-hydroxy-16-(indol-5-yloxy)-9α,11α-di(4-phenylbenzoyloxy)-17,18,19,20-tetranor-5-cis, 13-trans-prostadienoate (323mg.) was dissolved in a mixture of methanol (3.2ml.) and methylene dichloride (1.6ml.), N-chlorosuccinimide (53mg.) was added, and the mixture was stirred at room temperature for 3 hours. The reaction mixture was poured into aqueous sodium sulphate solution (10ml.), the resulting suspension was estracted with methylene dichloride (3 × 5ml.), the combined extracts were dried, and the solvent was evaporated to give methyl 16-(3-chloroindol-5-yloxy)-15-hydroxy-9α,11α-di-(4-phenylbenzoyloxy)-17,18,19,20-tetranor-5-cis,13-trans-prostadienoate, $R_F$ = 0.5 (ether), n.m.r. in deuteriochloroform:

δ 3.56, 3H, singlet, methyl ester 4.60, 1H, broad, C-15 proton 5.40, 4H, multiplet, protons at C5, 6, 9 and 11

5.88, 2H, multiplet, trans-olefin 6.7–8.2, 22H, multiplet, aromatic and indole C-2 protons 8.4, 1H, broad, indole NH proton.

c. 9α,11α,15-trihydroxy-16-(indol-5-yloxy)-17,18,19,20-tetranor-5-cis,13-trans-prostadienoic acid, identical with the product described in Example 4. In this case, in the preparation of the starting methyl ester, the enone was prepared as follows:

Dimethyl [2-oxo-3-(indol-5-yloxy)propyl]phosphonate (1.89g., 2 equivalents) and methyl 7-(2β-formyl-3α,5α-di-(4-phenylbenzoyloxy)-cyclopent-1α-yl]hept-5-cis-enoate (1.78g.) were dissolved in a mixture of toluene (50ml.) and t-butanol (10ml.), and cooled to 0° C. under nitrogen. Aqueous 1M sodium hydroxide solution (4.5ml; 1.5 equivalents) was added, and the two phase mixture was stirred vigorously, and allowed to warm to ambient temperature. The mixture was stirred overnight, then the organic phase was separated, washed with brine and dried, and the solvent was evaporated. The residue was chromatographed on silica (Florisil — trade mark) (150g.) using ether-ethyl acetate mixtures to elute methyl 16-(indol-5-yloxy)-15-oxo-9α,11α-di(4-phenylbenzoyloxy)-17,18,19,20-tetranor-5-cis, 13-trans-prostadienoate, identical with that obtained in Example 4.

d. 9α,11α,15-trihydroxy-16-(3-methylindol-5-yloxy)-17,18,19,20-tetranor-5-cis, 13-trans-prostadienoic acid, $R_F = 0.3$ and 0.4 (3% acetic acid in ethyl acetate). The mass spectrum showed $M^+ = 731.3850$ (calculated for $C_{37}H_{65}NO_6Si_4 = 731.3890$).

The methyl ester starting material was prepared by the process described in Example 4, modified as in (c) above, from 5-hydroxy-3-methylindole via the corresponding phosphonate, $R_F = 0.2$ (50% ethyl acetate in toluene) and the corresponding enone, $R_F = 0.75$ (25% ethyl acetate in toluene).

e. 9α,11α,15-trihydroxy-16-(indol-4-yloxy)-17,18,19,20-tetranor-5-cis, 13-trans-prostadienoic acid, $R_F = 0.28$ and 0.32 (3% acetic acid in ethyl acetate). The mass spectrum showed $M^+ = 717.3734$ (calculated for $C_{36}H_{63}NO_6Si_4 = 717.3734$).

The starting material was obtained from 4-hydroxyindole by the process described in (c) above via the corresponding phosphonate, $R_F = 0.23$ (ethyl acetate), n.m.r. in deuteriochloroform:

| | | |
|---|---|---|
| δ 7.0–7.3, | 3H, | ⎫ |
| 6.75, | 1H, | ⎬ indole protons. |
| 6.45, | 1H, | ⎭ |
| 4.82, | 2H, | —CO.CH$_2$O— | and the corresponding enone, $R_F = 0.24$ (15% ethyl acetate in toluene).

f. 9α,11α,15-trihydroxy-16-(4-methylpyrid-3-yloxy)-17,18,19,20-tetranor-5-cis, 13-trans-prostadienoic acid, $R_F = 0.31$ (mixture of ethyl acetate, methanol and acetic acid in the proportions 90, 10 and 3), $M^+ = 693.3741$, (calculated for $C_{34}H_{63}NO_6Si_4 = 693.3734$).

The starting material was prepared from 3-hydroxy-4-methylpyridine by the process described in (c) above, via the corresponding phosphonate, $R_F = 0.21$ (10% methanol in ethyl acetate), n.m.r. in deuteriochloroform:

| | | |
|---|---|---|
| δ 2.33, | 3H, | methyl |
| 4.85, | 2H, | —CO.CH$_2$O— |
| 7.15, | 1H, | ⎫ |
| 8.0–8.35, | 2H, | ⎬ pyridine protons. | and the corresponding enone, $R_F = 0.42$ (ethyl acetate).

g. 16-(1,2-dimethylindol-5-yloxy)-9α,11α,15-trihydroxy-17,18,19,20-tetranor-5-cis, 13-trans-prostadienoic acid, $R_F = 0.23$ and 0.30 (3% acetic acid in ethyl acetate), $M^+ = 745.4024$ (calculated for $C_{38}H_{67}NO_6Si_4 = 745.4047$).

The starting material was prepared by the process described in (c) above, via the appropriate phosphonate, $R_F = 0.25$ (ethyl acetate), m.p. 69°–71° C., and the corresponding enone, $R_F = 0.3$ (15% ethyl acetate in toluene), n.m.r. in deuteriochloroform:

δ2.34, 3H, methyl at indole C-2
3.55, 3H, N-methyl
4.72, 2H, —OCH$_2$CO—
6.10, 1H, C-3 proton of indole.

h. 9α,11α,15-trihydroxy-16-(indol-3-yl)-17,18,19,20-tetranor-5-cis, 13-trans-prostadienoic acid, $R_F = 0.42$ and 0.45(3% acetic acid in ethyl acetate), $M^+ = 701.3790$ (calculated for $C_{36}H_{63}NO_5Si_4 = 701.3785$).

The starting material was prepared by the process described under (c) above, via the appropriate phosphonate, $R_F = 0.22$ (ethyl acetate), n.m.r. in deuteriochloroform:

δ 3.0–3.7, 5H, aromatic protons
4.0, 2H, —CO.CH$_2$-indole, and the corresponding enone, $R_F = 0.11$ (20% ethyl acetate in toluene), n.m.r. in deuteriochloroform:

δ 3.58, 3H, methyl ester
3.98, 2H, —CO.CH$_2$ - indole.

i. 9α,11α,15-trihydroxy-16-(6-methylpyrid-2-yloxy)-17,18,19,20-tetranor-5-cis, 13-trans-prostadienoic acid, $R_F = 0.32$ (3% acetic acid in ethyl acetate). The mass spectrum showed $M^+ = 693.3726$ (calculated for $C_{34}H_{63}NO_6Si_4 = 693.3734$).

The starting material was prepared, by the process described in Example 4, from 2-hydroxy-6-methylpyridine, via dimethyl [3-(6-methylpyrid-2-yloxy)-2-oxopropyl]phosphonate, $R_F = 0.35$ (ethyl acetate), n.m.r. in deuteriochloroform:

| | | |
|---|---|---|
| δ 7.46, | 1H, | ⎫ |
| 6.64, | 1H, | ⎬ pyridine protons. |
| 6.72, | 1H, | ⎭ |
| 2.36, | 3H, | methyl. | and the corresponding enone was prepared as follows:
n-Butyl-lithium (71μl. of a 2.29M solution in hexane) was added to a solution of N-isopropylcyclohexylamine (37.5μl.) in 1,2-dimethoxyethane (0.5ml.) at −78° C. under argon. The mixture was stirred at −78° C. for 15 minutes, and then treated with a solution of dimethyl [3-(6-methylpyrid-2-yloxy)-2-oxopropyl]phosphonate (51mg.) in 1,2-dimethoxyethane (2ml.) at −78° C. for a further 15 minutes. Powdered methyl 7-[2β-formyl-3α,5α-di(4-phenylbenzoyloxy)cyclopent-1α-yl]hept-5-cis-enoate (78.5mg.) was added, the cooling bath was removed and the mixture was stirred overnight at room temperature. Glacial acetic acid (100μl.) and water (100μl.) were added, and the 1,2-dimethoxyethane was evaporated at room temperature under reduced pressure. The residue was partitioned between ethyl acetate (2 × 10ml.) and brine (5 ml.), and the ethyl acetate layer was separated. Evaporation of the solvent, and chromatography of the residue on silica gel yielded the required enone, methyl 16-(6-methylpyrid-2-yloxy)-15-oxo-9α,11α-di-(4-phenylbenzoyloxy)-17,18,19,20-tetranor-5-cis,13-trans-prostadienoate, $R_F$= 0.26 (20% ethyl acetate in toluene).

j. 9α,11α,15-trihydroxy-16-(2-methylpyrid-3-yloxy)-17,18,19,20-tetranor-5-cis, 13-trans-prostadienoic acid, $R_F$= 0.85 (2% acetic acid in methanol). The mass spectrum showed $M^+$ = 693.3727 (calculated for $C_{34}H_{63}NO_6Si_4$= 693.3734).

The starting material was prepared by the process described in Example 4 from 3-hydroxy-2-methylpyridine, via dimethyl [2-oxo-3-(2-methylpyrid-3-yloxy)-propyl]phosphonate, $R_F$= 0.31 (10% methanol in ethyl acetate), n.m.r. in deuteriochloroform:

δ 2.55, 3H, methyl 4.85, 2H, —CO . CH₂O—

7.0–7.15, 2H, ⎫
8.15, 1H,  ⎬ pyridine protons, and the corresponding enone was prepared as follows:

Sodium hydride (60% dispersion in oil; 15.6mg.) was washed free of oil with dry pentane, then suspended in dry 1,2-dimethoxyethane (2ml.). A solution of the phosphonate (123mg.) in dry 1,2-dimethoxyethane (3ml.) was added slowly at ambient temperature. The mixture was stirred for 15 minutes, then a solution of methyl 7-[2β-formyl-3α,5α-di-(4-phenylbenzoyloxy)-cyclopent-1α-yl]hept-5-cis-enoate (189mg.) in dry 1,2-dimethoxyethane (2ml.) was added slowly. The mixture was stirred overnight, then adjusted to pH 7 with 2N hydrochloric acid, and the mixture was evaporated to dryness. The residue was partitioned between water and ethyl acetate, and the aqueous layer was extracted with more portions of ethyl acetate. The combined ethyl acetate extracts were washed with brine and dried, and the solvent was evaporated, to yield a residue which was purified by preparative layer chromatography with a mixture of toluene, ethyl acetate and methanol in the proportions 12:8:1, to give methyl 16-(2-methylpyrid-3-yloxy)- 15-oxo-9α,11α-di-(4-phenylbenzoyloxy)-17,18,19,20-tetranor- 5-cis, 13-trans-prostadienoate as an oil, $R_F$= 0.35 (12:8:1, toluene : ethyl acetate : methanol).

The compounds shown in the following table were prepared in a similar manner to that described in (j) above, via the phosphonates and enones as shown:

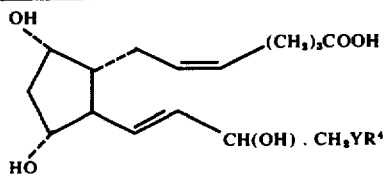

| No. | Y | R⁴ | Mass spectrum[1] Found | Calculated |
|---|---|---|---|---|
| 1 | O | 4-methylquinol-2-yl | 743.3846 | 743.3890 |
| 2 | O | quinol-3-yl | 729[2] | 729.3734 |
| 3 | O | quinol-6-yl | 729.3738 | 729.3734 |
| 4 | O | 6-methoxy-2-methyl-pyrimid-4-yl | 724.3743 | 724.3792 |
| 5 | O | 6-methylpyrid-3-yl | 693.3727 | 693.3734 |
| 6 | O | 6-chloropyrid-2-yl | 698.2940[3] | 698.2953 |
| 7 | O | pyrid-2-yl | 679.3556 | 679.3577 |
| 8 | O | 2-chloropyrid-4-yl | 713.3156 | 713.3187 |
| 9 | O | trichloro-methoxypyrid-2-yl[4] | 796.2285 | 796.2280 |
| 10 | CH₂ | indolin-1-yl | 717.4085 | 717.4098 |

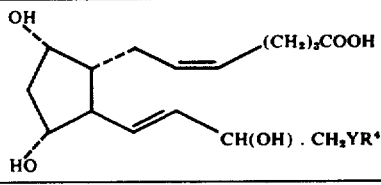

[1]measured on mixed C-15 epimers, except for compound 9 which was for the less polar epimer.

[2]not accurately mass measured. This compound may be further characterised by $R_F$ = 0.09 and 0.13 (3% acetic acid in ethyl acetate) and n.m.r. in a mixture of deuteriochloroform and deuteriated acetone:

δ 8.62, 1H, quinolyl C-2 proton,
7.85–8.05, 1H, quinolyl C-4 proton,
7.30–7.75, 4H, quinolyl C-5 to C-8 protons,
5.1–6.4, 8H, olefinic and exchangeable OH protons
4.5–4.7, 1H, C-15 proton.

[3](M-CH₃)⁺ ion

[4]This compound prepared from methyl 15-hydroxy-9α,11α-di-(4-phenylbenzoyloxy)-16-(3,4,5,6-tetrachloropyrid-2-yloxy)-17,18,19,20-tetranor-5-cis, 13-trans-prostadienoate, one chlorine-being replaced by methoxy during the reacton with potassium hydroxide in methanol.

| No. | Phosphate | Enone |
|---|---|---|
| 1 | $R_F$ = 0.62 (10% methanol/ethyl acetate) | $R_F$ = 0.74 (ether) |
| 2 | $R_F$ = 0.5 (10% methanol/ethyl acetate) | $R_F$ = 0.64 (50% ether/toluene) |
| 3 | $R_F$ = 0.18 (10% methanol/ethyl acetate) | $R_F$ = 0.45 (50% ethyl acetate/toluene) |
| 4 | $R_F$ = 0.48 (10% methanol/ethyl acetate) | $R_F$ = 0.6 (25% ethyl acetate/toluene) |
| 5 | $R_F$ = 0.3 (10% methanol/ethyl acetate) | $R_F$ = 0.5 (50% ethyl acetate/toluene) |
| 6 | $R_F$ = 0.4 (10% methanol/ethyl acetate | $R_F$ = 0.5 (25% ethyl acetate/toluene) |
| 7 | $R_F$ = 0.3 (10% methanol/ethyl acetate) | $R_F$ = 0.4 (25% ethyl acetate/toluene) |
| 8 | m.p. 63–65° C. | $M^+$ = 797.2728 (797.2755) |
| 9 | $R_F$ = 0.45 (5% methanol/ethyl acetate)* | $R_F$ = 0.2(5% ethyl acetate/methylene chloride)* |
| 10 | $R_F$ = 0.3 (10% methanol/ethyl acetate)* | $R_F$ = 0.6(50% ethyl acetate/toluene) |

*These are 3,4,5,6-tetrachloropyrid-2-yl intermediates - see footnote [4] to the first part of the table.

k. 9α,11α,15-trihydroxy-15-(1-methylbenzimidazol-2-yl)-16,17,18,19,20-pentanor-5cis, 13-trans-prostadienoic acid, $R_F$= 0.11 (15% methanol in methylene dichloride). Mass spectrum showed $M^+$ = 702.3742 (calculated for $C_{35}H_{63}N_2O_5Si_4$= 702.3737).

The starting material was prepared, by the process described in (c) above, from methyl 1-methylbenzimidazole-2-carboxylate via dimethyl [2-oxo-2-(1-methylbenzimidazol-2-yl)ethyl]phosphonate, $R_F$= 0.31 (10% methanol in methylene dichloride), n.m.r. in deuteriochloroform:

δ 4.2, 3H, methyl
7.5–8.1, 4H, aromatic.

and the corresponding enone, $R_F$= 0.41 (20% ethyl acetate in toluene), n.m.r. in deuteriochloroform:

δ 3.4, 3H, methyl ester
4.2, 3H, benzimidazole methyl

In the reduction of the enone, aluminium tri-isopropoxide at 50°C. was used in place of di-isobornyloxy aluminum isopropoxide.

l. 16-(6-chloropyridazin-3-yloxy)-9α,11α,15-trihydroxy-17,18,19,20-tetranor-5-cis, 13-trans-prostadienoic acid, $R_F$= 0.5 (1% acetic acid, 9% methanol, 90% ethyl acetate), $M^+$= 714.3096 (calculated for $C_{32}H_{59}ClN_2O_6Si_4$= 714.3139)

The starting material was prepared, by the process described in (c) above, from 6-chloro-3-hydroxypridazine, via the corresponding phosphonate, $R_F$= 0.5 (3% methanol in methylene dichloride), n.m.r. in deuteriochloroform:

δ 7.0–7.6, 2H, pyridazine protons
5.3, 2H, —CO.CH$_2$O— and the corresponding enone, $R_F$= 0.25 (15% ethyl acetate in toluene), n.m.r. in deuteriochloroform:

δ 5.35, 2H, —CO.CH$_2$O—
3.55, 3H, methyl ester.

m. 9α,11α,15-trihydroxy-16-(7-methyindol-5-yloxy)-17,18,19,20-tetranor-5-cis, 13-trans-prostadienoic acid, $R_F$= 0.30 and 0.35 (3% acetic acid in ethyl acetate), $M^+$ = 731.3849 (calculated for $C_{37}H_{65}NO_6Si_4$= 731.3890).

The starting material was prepared, by the process described in (c) above, from 5-hydroxy-7-methylindole via the corresponding phosphonate, $R_F$= 0.2 (50% ethyl acetate in toluene), n.m.r. in deuteriochloroform:

δ 6.5–7.0, 3H, indole protons at C-2, 4 and 6,
6.4, 1H, indole C-3 proton,
4.6, 2H, —CO.CH$_2$O—,
2.5, 3H, indole 7-methyl, and the corresponding enone, $R_F$= 0.35 (15% ethyl acetate in toluene), n.m.r. in deuteriochloroform:

δ 4.7, 2H, —CO.CH$_2$O—
2.4, 3H, indole 7-methyl.

EXAMPLE 6

To a solution of the more polar C-15 epimer of 9α,11α,15-trihydroxy-16-(indol-5-yloxy)-17,18,19,20-tetranor-5-cis, 13-trans-prostadienoic acid (10mg.) in ethanol (2ml.) at 0°C. was added an excess of a solution of diazomethane in ether. After 10 minutes, the solvents were evaporated to give a single C-15 epimer of methyl 9α,11α,15-trihydroxy-16-(indol-5-yloxy)-17,18,19,20-tetranor-5-cis, 13-trans-prostadienoate which was purified by thin layer chromatography, $R_F$= 0.35 (ethyl acetate). The n.m.r. spectrum in deuterated acetone showed the following characteristic absorptions (δ values):

6.7–7.4, 5H, aromatic protons and >NH
6.4, 1H, indole C-3 proton
3.6, 3H, methyl ester.

The mass spectrum showed $M^+$ = 731.3864 (calculated for $C_{37}H_{65}NO_6Si_4$ = 731.3889).

The above process was repeated, using the appropriate prostanoic acid as starting material, to give the following compounds:

a. less polar C-15 epimer of methyl 9α,11α,15-trihydroxy-16-(indol-5-yloxy)-17,18,19,20-tetranor-5-cis, 13-trans-prostadienoate, $R_F$ = 0.46 (ethyl acetate). The n.m.r. spectrum was identical to that of the more polar epimer described above.

b. methyl 16-(4,6-dimethylpyrid-2-yloxy)-9α, 11α,15-trihydroxy-17,18,19,20-tetranor-5-cis, 13-trans-prostadienoate, $R_F$ = 0.2 and 0.3 (3% acetic acid in ethyl acetate).

c. methyl 9α,11α,15-trihydroxy-16-(pyrid-4-yloxy)-17,18,19,20-tetranor-5-cis, 13-trans-prostadienoate (mixed C-15 epimers), $M^+$ = 621.3306 (calculated for $C_{31}H_{55}NO_6Si_3$ = 621.3337).

d. methyl 16-(2,6-dimethylpyrid-4-yloxy)-9α,11α,15-trihydroxy-17,18,19,20-tetranor-5-cis, 13-trans-prostadienoate, $M^+$ = 649.3652 (calculated for $C_{33}H_{59}NO_6Si_3$ = 649.3650).

EXAMPLE 7

A solution of methyl 15-hydroxy-16-(6-methoxypyrid-3-yloxy)-9α,11α-di-(4-phenylbenzoyloxy)-17,18,19,20-tetranor-5-cis, 13-trans-prostadienoate (159mg.) in anhydrous methanol (10ml.) was stirred with powdered potassium carbonate (100mg.) under argon for 18 hours. The solution was acidified to pH 7 with glacial acetic acid and the solvent was removed under reduced pressure. The residue was partitioned between ethyl acetate (2 × 20ml.) and water (10ml.), and the ethyl acetate phases were combined, dried and evaporated to dryness. Preparative layer chromatography of the residue gave methyl 9α,11α,15-trihydroxy-16-(6-methoxypyrid-3-yloxy)-17,18,19,20-tetranor-5-cis,13-trans-prostadienoate, as a mixture of C-15 epimers, $R_F$ = 0.27 (ethyl acetate). The mass spectrum showed $M^+$ = 651.3430 (calculated for $C_{32}H_{57}NO_7Si_3$ = 651,3443).

The ester used as starting material was prepared by the process described in Example 5(i), via the corresponding phosphonate, $R_F$ = 0.21 (ethyl acetate), n.m.r. in deuteriochloroform:

| δ 7.85, | 1H, | pyridine protons. |
|---|---|---|
| 7.30, | 1H, | |
| 6.70, | 1H, | |
| 3.90, | 3H, | methoxy. | prepared by the process described in Example 4, and the corresponding enone, $R_F$ = 0.27 (20% ethyl acetate in toluene).

The following compounds (as mixed C-15 epimers) were prepared in a similar manner:

a. methyl 16-(5-chloropyrid-3-yloxy)-9α,11α,15-trihydroxy-17,18,19,20-tetranor-5-cis, 13-trans-prostadienoate, $R_F$ = 0.36 (ethyl acetate), $M^+$ = 655.2954 (calculated for $C_{31}H_{54}ClNO_6Si_3$ = 655.2947).

The prostadienoic acid starting material was obtained from 5-chloro-3-hydroxypyridine by the process described above via the appropriate phosphonate, $R_F$ = 0.17 (ethyl acetate) and the corresponding enone, $R_F$ = 0.55 (10% methanol in toluene).

The phosphonate was prepared from ethyl 2,5-dichloropyrid-3-yloxyacetate as follows:

A solution of ethyl (2,5-dichloropyrid-3-yloxy)-acetate (200mg.) in glacial acetic acid (8ml.) was stirred overnight under reflux with acid washed zinc powder (1.0g.). The solution was cooled and filtered and the filtrate was evaporated to dryness. The residue was purified by chromatography on silica gel to yield ethyl(5-chloropyrid-3-yloxy)acetate, m.p. 38°–40° C. (ether-pentane).

b. methyl 16-(2,5-dichloropyrid-3-yloxy)-9α,11α,15-trihydroxy-17,18,19,20-tetranor-5-cis,13-trans-prostadienoate, $R_F$ = 0.30 (ethyl acetate).

The prostadienoic acid starting material was obtained from 2,5-dichloro-3-hydroxypyridine by the process described above, via the appropriate phosphonate, $R_F = 0.32$ (50% ethyl acetate in methylene dichloride), n.m.r. in deuteriochloroform:

δ 8.03, 1H,  } pyridine protons,
7.31, 1H, and the corresponding enone, $R_F = 0.43$ (25% ethyl acetate in toluene).

The phosphonate was prepared from 2,5-dichloro-3-hydroxypyridine, which was itself prepared as follows:

A mixture of 5-chloro-2,3-dihydroxypyridine (1.0g.) and phosphoryl chloride (10ml.) was heated overnight at 180° C. in a sealed tube. The phosphoryl chloride was distilled off, and the residue was chromatographed, to give 2,5-dichloro-3-hydroxypyridine, m.p. 160°–161° C. (ethyl acetate - petrol).

c. methyl 9α,11α,15-trihydroxy-15-(6-methoxypyrid-3-yl)-16,17,18,19,20-pentanor-5-cis, 13-trans-prostadienoate, $R_F = 0.30$ (ethyl acetate).

The prostadienoic acid starting material was prepared from methyl 6-methoxynicotinate by the process described in Example 5(c), via the appropriate phosphonate, $R_F = 0.26$ (ethyl acetate), n.m.r. in deuteriochloroform:

δ 8.85, 1H,
8.20, 1H, } pyridine protons.
6.82, 1H, 4.06, 3H, methoxy.

and the corresponding enone, $R_F = 0.57$ (20% ethyl acetate in toluene).

d. methyl 9α,11α,15-trihydroxy-16-(1-methylindolin-5-yloxy)-17,18,19,20-tetranor-5-cis, 13-trans-prostadienoate, $R_F = 0.3$ (ethyl acetate), $M^+ = 675.3785$ (calculated for $C_{35}H_{61}NO_6Si_3 = 675.3807$).

The prostanoic acid starting material was obtained via the appropriate phosphonate, which was prepared by hydrogenation of the corresponding indole phosphonate as follows:

A solution of dimethyl[2-oxo-3-(indol-5-yloxy)-propyl]-phosphonate (250mg.) in glacial acetic acid (5ml.) was hydrogenated for 3 hours in the presence of 5% palladium-on-charcoal (250mg.). The catalyst was filtered off, the filtrate was evaporated to dryness, and the residue was purified by thin-layer chromatography, $R_F = 0.1$ (ethyl acetate) n.m.r. in deuteriochloroform:

δ 2.65, 3H, N-methyl
2.7–2.9, 2H, } C-2 and C-3 protons of indoline,
3.08–3.28, 2H, and the corresponding enone, $R_F = 0.42$ (25% pentane in ether), n.m.r. in deuteriochloroform:

δ 2.6, 3H, N-methyl
3.5, 3H, methyl ester
4.48, 2H, —CO.CH₂O— e. methyl 16-(2-chloropyrid-3-yloxy)-9α,11α,15-trihydroxy-17,18,19,20-tetranor-5cis,13-trans-prostadienoate $R_F = 0.26$ (ethyl acetate), $M^+ = 655.2948$ (calculated for $C_{31}H_{54}ClNO_6Si_3 = 655.2947$).

The prostanoic acid starting material was prepared from 2-chloro-3-hydroxypyridine by the process described in Example 4, via the corresponding phosphonate, $R_F = 0.3$ (ethyl acetate), n.m.r. in deuteriochloroform:

δ 7.95–8.1, 1H, } pyridine protons,
7.1–7.3, 2H, 4.8, 2H, —CO.CH₂O— and the corresponding enone, $R_F = 0.2$ (20% ethyl acetate in toluene), n.m.r. in deuteriochloroform:

δ 5.25–5.6, 4H, C-9, C-11 and cis-olefinic protons,
4.8, 2H, —CO.CH₂O—,
3.54, 3H, methyl ester.

EXAMPLE 8

A solution of methyl 15-hydroxy-16-(indol-5-yloxy)-9α,11α-di-(4-phenylbenzoyloxy)-17,18,19,20-tetranor-5-cis, 13-trans-prostadienoate (85mg.) in dry 1,2-dimethoxyethane (5ml.) was added to a suspension of lithium aluminium hydride (100mg.) in dry 1,2-dimethoxyethane (5ml.). After 1 hour, water was added, the mixture was filtered and the filtrate was evaporated to dryness. The residue was partitioned between water and ethyl acetate, the ethyl acetate layer was separated and dried, the solvent was evaporated, and the residue was purified by thin layer chromatography, eluting with 5% methanol in ethyl acetate, to give a mixture of C-15 epimers of 9α,11α,15-trihydroxy-16-(indol-5-yloxy)-17,18,19,20-tetranor-5-cis,13-trans-prostadienol,$R_F = 0.35$ (5% methanol in ethyl acetate). The n.m.r. spectrum in deuterated acetone showed the following characteristic absorptions (δ

6.7–7.4, 4H, aromatic protons
6.35, 1H, indole C-3 proton
5.65–5.8, 2H, trans olefinic protons
5.15–5.65, 2H, cis olefinic protons The mass spectrum showed $M^+ = 703.3908$ (calculated for $C_{36}H_{65}O_5NSi_4 = 703.3940$).

EXAMPLE 9

The process described in Example 4 was repeated using methyl 15-hydroxy-15-(indol-2-yl)-9α, 11α-di-(4-phenylbenzoyloxy)-16,17,18,19,20-pentanor-5-cis-prostenoate as the starting material to give 9α,11α,15-trihydroxy-15-(indol-2-yl)-16,17,18,19,20-pentanor-5-cis-prostenoic acid, mixed C-15 epimers, $R_F = 0.16$ (15% ethyl acetate in toluene), $M^+ = 631.3538$ (calculated for $C_{35}H_{57}NO_5Si_3 = 631.3544$).

The methyl ester used as starting material was prepared from ethyl indole-2-carboxylate by the process described in Example 5(c) via dimethyl [2-oxo-2-(indol-2-yl)-ethyl]phosphonate, m.p. 133°–134° C., and the corresponding enone, methyl 15-(indol-2-yl)-15-oxo-9α,11α-di(4-phenylbenzoyloxy)-16,17,18,19,20-pentanor-5cis,13-trans-prostadienoate, m.p. 161°–165° C., which was reduced as follows:

To a solution of the enone (30mg.) in a mixture of isopropanol (5ml.) and 1,2-dimethoxyethane (5ml.) was added sodium borohydride (30mg.). After 15 minutes, the solution was adjusted to pH 4 with glacial acetic acid and the solvents were evaporated. The residue was partitioned between ethyl acetate and a 1:1 mixture of saturated brine and water, and the ethyl acetate layer was separated and dried. Evaporation of the solvent gave the required starting material, methyl 15-hydroxy-15-(indol-2-yl)-9α,11α-di(4-phenylbenzoyloxy)-16,17,18,19,20-pentanor-5-cis-prostenoate.

EXAMPLE 10

The process described in Example 4 was repeated, using methyl 11α,15-dihydroxy-16-(indol-5-yloxy)-9α-(4-phenylbenzoyloxy)-17,18,19,20-tetranor-13-trans-prostenoate in place of methyl 15-hydroxy-16-(indol-(indol-5-yloxy)-9α,11α-di(4-phenylbenzoyloxy)-17,18,19,20-tetranor-5-cis,13-trans-prostadienoate, to give the C-15 epimers of 9α,11α,15-trihydroxy-16-(indol-5-yloxy)-17,18,19,20-tetranor-13-trans-prostenoic acid, $R_F = 0.3$ and 0.45 (3% acetic acid in ethyl acetate). The n.m.r. spectrum of the more polar C-15 epimer, in deuterated acetone, showed the following characteristic absorptions ($\delta$ values):

| 3.9, | 3H, | multiplet, | C-16 and 1 >CH . OH protons |
| 4.2, | 1H, | multiplet, | >CH . OH |
| 4.45, | 1H, | multiplet, | |
| 5.7, | 2H, | multiplet, | olefinic protons |
| 6.4, | 1H, | singlet, | indole C-3 proton |
| 6.8, | 1H, | double doublet (J = 9 and 3Hz), indole C-6 proton |
| 7.1, | 1H, | doublet (J = 3Hz), indole C-4 proton |
| 7.3, | 2H, | multiplet, | indole C-2 and C-7 protons |

$M^+ = 719.3924$ (calculated for $C_{36}H_{65}NO_6Si_4 = 719.3890$).

The methyl 11α,15-dihydroxy-16-(indol-5-yloxy)-9α-(4-phenylbenzoyloxy)-17,18,19,20-tetranor-13-trans-prostenoate used as starting material in the above process may be prepared as follows:

To a solution of 7-[2β-dimethoxymethyl-5α-hydroxy-3α-(tetrahydropyran-2-yloxy)cyclopent-1α-yl]hept-5-cis-enoic acid (4.9g.) (prepared as described in the latter part of Example 4) in ether (20ml.) was added an excess of a solution of diazomethane in ether. After 20 minutes at room temperature, excess diazomethane was evaporated in a stream of argon, and the ether solution was washed with saturated sodium bicarbonate solution (5ml.). The organic solution was dried and evaporated to dryness to give methyl 7-[2α-dimethoxymethyl-5α-hydroxy-3α-(tetrahydropyran-2-yloxy)cyclopent-1α-yl]hept-5-cis-enoate as a clear oil $R_F = 0.6$ (5% methanol in methylene dichloride). The n.m.r. spectrum in deuteriochloroform showed the following features ($\delta$ values):

3.4, 6H, singlet, —CH(OC$\underline{H}_3$)$_2$
3.6, 3H, singlet, —COOC$\underline{H}_3$
4.7, 1H, broad singlet, —C$\underline{H}$(OCH$_3$)$_2$
5.45, 2H, multiplet, olefinic protons.

Methyl 7-[2β-dimethoxymethyl-5α-hydroxy-3α-tetrahydropyran- 2-yloxy)cyclopent-1α-yl]hept-5-cis-enoate (4.3g.) was dissolved in dry pyridine (50ml.) under argon, the solution was treated with p-phenylbenzoyl chloride (4.65g.) and the mixture was stirred for 17 hours. Water (2.5ml.) was then introduced and stirring was continued for 2 hours. The mixture was evaporated under reduced pressure and toluene was added to assist azeotropic removal of the pyridine. The residue was partitioned between toluene (300ml.) and saturated sodium bicarbonate solution (150ml.), the whole mixture was filtered through kieselguhr (Hyflo — trade mark) and the organic phase was separated. The aqueous layer was extracted with toluene (150ml.), the organic extracts were combined, washed with brine (100ml.), dried over sodium sulphate, and filtered, and the solvent was evaporated to give methyl 7-[2α-dimethoxymethyl-5α-(4-phenylbenzoylozy)-3α-(tetrahydropyran-2-yloxy)cyclopent-1α-yl]hept-5-cis-enoate as a clear oil, $R_F = 0.8$ (ether), whose n.m.r. spectrum in deuteriochloroform showed the following features ($\delta$ values):

3.42, 6H, doublet, —CH(OC$\underline{H}_3$)$_2$
3.6, 3H, singlet, —COOC$\underline{H}_3$
5.4, 2H, multiplet, olefinic protons
7.2–8.2, 9H, multiplet, aromatic protons.

A solution of methyl 7-[2β-dimethoxymethyl-5α-(4-phenylbenzoyloxy)-3α-(tetrahydropyran-2-yloxy)cyclopent-1α-yl]hept-5-cis-enoate (6.49g.) in dry methanol (140ml.) was stirred under argon at room temperature with toluene-p-sulphonic acid (9.4ml. of a 1% solution of anhydrous toluene-p-sulphonic acid in dry tetrahydrofuran) for 2.5 hours. Pyridine (5ml.) and toluene (40ml.) were added, and the solvents were evaporated under reduced pressure. The residue was partitioned between ethyl acetate (100ml.) and water (50ml.), and the organic phase was separated, washed successively with saturated sodium bicarbonate (2 × 30ml.) and saturated brine (30ml.) and dried, and the solvent was evaporated to give methyl 7-[2β-dimethoxymethyl-3α-hydroxy-5α-(4-phenylbenzoyloxy)cyclopent-1α-yl]hept-5-cis-enoate as a clear oil, $R_F = 0.4$ (ether), whose n.m.r. spectrum in deuteriochloroform showed the following definitive features ($\delta$ values):

3.42, 6H, doublet, —CH(OC$\underline{H}_3$)$_2$
3.52, 3H, singlet, —COOC$\underline{H}_3$
4.25, 1H, multiplet, >CH.OH
4.35, 1H, doublet, —C$\underline{H}$(OCH$_3$)$_2$
5.35, 3H, multiplet, olefinic protons plus >CH.OCO—
7.2–8.2, 9H, multiplet, aromatic protons.

A solution of methyl 7-[2β-dimethoxymethyl-3α-hydroxy-5α-(4-phenylbenzoyloxy)-cyclopent-1α-yl]hept-5-cis-enoate (1g.) in ethyl acetate (40ml.) was stirred overnight in an atmosphere of hydrogen at room temperature and pressure in the presence of 5% palladium-on-charcoal (500mg.). The catalyst was removed by filtration through kieselguhr (Hyflo — trade mark) and the solvent was evaporated from the filtrate to give methyl 7-[2β-dimethoxymethyl-3α-hydroxy-5α-(4-phenylbenzoyloxy)-cyclopent-1α-yl]heptanoate, $R_F = 0.4$ (ether). The n.m.r. spectrum in deuteriochloroform had the following characteristic signals ($\delta$ values);

3.45, 6H, doublet, —CH(OC$\underline{H}_3$)$_2$
3.6, 3H, singlet, —COOC$\underline{H}_3$
4.3, 1H, multiplet, >C$\underline{H}$.OH
4.35, 1H, doublet, —C$\underline{H}$(OCH$_3$)$_2$
5.42, 1H, multiplet, >C$\underline{H}$.OCO—
7.2–8.2, 9H, multiplet, aromatic protons.

Methyl 7-[2α-dimethoxymethyl-3α-hydroxy-5α-(4-phenylbenzoyloxy)-cyclopent-1α-yl]heptanoate (400mg.) was vigorously stirred under argon for 10 minutes in a two-phase system consisting of 2% isopropanol in chloroform (16ml.) and concentrated hydrochloric acid (8ml.). The total reaction mixture was poured into an excess of saturated sodium bicarbonate solution and the organic layer was separated. The aqueous solution was extracted with ethyl acetate (3 × 50ml.) and the combined organic extracts were washed with brine (50ml.) and dried, and evaporated to give methyl 7-[2β-formyl-3α-hydroxy-5α-hydroxy-5α-(4-phenylbenzoyloxy)cyclopent-1α-yl]heptanoate as a clear oil, $R_F = 0.2$ (ether).

Dimethyl [2-oxo-3-(indol-5-yloxy)propyl]phosphonate (600mg., 2.5 equivalents) and methyl 7-[2β-formyl-3α-hydroxy-5α-(4-phenylbenzoyloxy)-cyclopent-1α-yl]heptanoate (400mg. 1 equivalent) were suspended under argon in a mixture of toluene (20ml.) and t-butanol (4ml). Aqueous 1M sodium hydroxide solution (1.84ml., 2.3 equivalents) was added and the two phase mixture was stirred vigorously for 3 hours. The reaction mixture was shaken with ethyl acetate (20ml.) and saturated brine (20ml.), and the organic layer was separated. The aqueous layer was extracted with ethyl acetate (2 × 20ml.), the combined organic extracts were dried, and the solvent was evaporated. Preparative thin layer chromatography gave methyl 11α-hydroxy-16-(indol-5-yloxy)-15-oxy-9α-(4-phenylbenzoyloxy)-17,18,19,20-tetranor-13-trans-prostenoate as a clear oil, $R_F = 0.3$ (25% ethyl acetate in toluene).

The process described in Example 4 was repeated using methyl 11α-hydroxy-16-(indol-5-yloxy)-15-oxo-9α-(4-phenylbenzoyloxy)-17,18,19,20-tetranor-13-trans-prostenoate in place of methyl 16-(indol-5-yloxy)-15-oxo-9α,11α-di-(4-phenylbenzoyloxy)-17,18,19,20-tetranor-5-cis,13-trans-prostadienoate, to give the C-15 epimers of methyl 11α,15-dihydroxy-16-(indol-5-yloxy)-9α-(4-phenylbenzoyloxy)-17,18,19,20-tetranor-13-trans-prostenoate, $R_F = 0.1$ (25% ethyl acetate in toluene), whose n.m.r. spectrum in deuteriochloroform showed the following features (δ values):

3.6, 3H, singlet, —COOC$\underline{H}_3$
4.0, 2H, multiplet, —CH(OH).C$\underline{H}_2$O-
4.6, 2H, multiplet, 2 × >C$\underline{H}$.OH
5.4, 1H, multiplet, >C$\underline{H}$.OCO—
5.8, 2H, multiplet, olefinic protons
6.4, 1H, broad singlet, indole C-3 proton
6.8-8.2, 14H, remainder of the aromatic protons plus >N—$\underline{H}$

EXAMPLE 11

The process described in Example 4 was repeated. using methal 11α,15-dihydroxy-16-(indol-5-yloxy)-2-methyl-9α-(4-phenylbenzoyloxy)-17,18,19,20-tetranor-5-cis,13-trans-prostadienoate as the starting material, to give 9α,11α,15-trihydroxy-16-(indol-5-yloxy)-2-methyl-17,18,19,20-tetranor-5-cis,13-trans-prostadienoic acid which was separaed into more polar and less polar epimers on preparative thin layer chromatography $R_F = 0.25$ and 0.33 (3% acetic acid in ethyl acetate). The mass spectrum showed M$^+$ = 731.3900 (calculated for $C_{37}H_{65}NO_6Si_4$ = 731.3890).

The starting material was prepared by the process described in Example 10 using (4-carboxy-3-methylbutyl)triphenylphosphonium bromide instead of (4-carboxybutyl)triphenyl-phosphonium bromide, and omitting the hydrogenation step in order to preserve the 5-cis double bond, via the following intermediates:

7-[2β-dimethoxymethyl-5α-hydroxy-3α-(tetrahydropyran-2-yloxy)cyclopent-1α-yl]-2-methyl-5-cis-heptenoic acid, $R_F = 0.26$ (5% methanol in methylene chloride), n.m.r. in deuterated chloroform:

δ 1.1-1.2, 3H, doublet, C$\underline{H}_3$-CH<
3.35 6H, singlet, —CH(OC$\underline{H}_3$)$_2$ Methyl 7-[2β-dimethoxyethyl-5α-hydroxy-3α-(tetrahydropyran-2-yloxy)cyclopent-1α-yl]-2-methyl-5-cis-heptenoate, $R_F = 0.33$ (5% methanol in methylene chloride), n.m.r. in deuterated chloroform:

δ 1.1-1.2, 3H, doublet, C$\underline{H}_3$.CH<
3.35, 6H, singlet, —CH(OC$\underline{H}_3$)$_2$
3.65, 3H, singlet, —COOC$\underline{H}_3$ Methyl 7-[2β-dimethoxymethyl-5α-(4-phenylbenzoyloxy)3α-(tetrahydropyran-2-yloxy)cyclopent1α-yl]-2-methyl-5-cis-heptenoate, $R_F = 0.55$ (ether), n.m.r. in deuterated chloroform:

δ 0.9-1.1, 3H, C$\underline{H}_3$—CH<
3.4, 6H, —CH(OC$\underline{H}_3$)$_2$
3.6, 3H, —COOC$\underline{H}_3$
7.2-8.3, 9H, aromatic protons.

Methyl 7-[2β-dimethoxymethyl-3α-hydroxy-5α-(4-phenylbenzoyloxy)cyclopent-1α-yl]-2-methyl-5-cis-heptenoate, $F_F = 0.42$ (ether), n.m.r. in deuterated chloroform:

δ 0.9-1.2, 3H, C$\underline{H}_3$CH<
3.4, 6H, —CH(OC$\underline{H}_3$)$_2$
3.6, 3H, —COOC$\underline{H}_3$.

Methyl 7-[2β-formyl-3α-hydroxy-5α-(4phenylbenzoyloxy)cyclopent-1αyl]-2-methyl-5-cis-heptenoate, $R_F = 0.48$ (ether).

Methyl 11α-hydroxy-16-(indol-5-yloxy)-15-oxo-9α-(4-phenylbenzoyloxy)-17,18,19,20-tetranor -5-cis,-13-trans prostadienoate, $R_F = 0.34$ (25% ethyl acetate in toluene), n.m.r. in deuterated chloroform:

δ 0.7-1.0, 3H, C$\underline{H}_3$CH<
3.55, 3H, —CO$_2$C$\underline{H}_3$
6.4, 1H, indole C-3 proton Methol 11α,15-dihydroxy-16-(indol-5-yloxy)-9α-(4-phenylbenzoyloxy)-17,18,19,20-tetranor-5-cis,13-trans-prostadienoate, $R_F = 0.17$ (5% methanol in methylene chloride), n.m.r. in deuterated chloroform:

δ 5.2-5.5, 3H, cis olefinic and C-9 protons
5.7-5.9, 2H, trans olefinic protons.

EXAMPLE 12

A mixture of the more polar C-15 epimer of methyl 9α,11α,15-trihydroxy-16-(indol-5-yloxy)-17,18,19,20-tetranor-5-cis,13-trans-prostadienoate and the more polar C-15 epimer of methyl 9α,11α,15-trihydroxy-16-(indol-5-yloxy)-17,18,19,20-tetranor-5-trans, 13-trans-prostadienoate was separated by thin layer chromatography on silica plates which had been pretreated by being sprayed liberally with a 4% solution of silver nitrate in 1:1 methanol/water, allowed to dry one half hour at room temperature, and oven-dried at 100° C. to reactivate the silica, to give the 5-trans-compound, $R_F = 0.32$ (40% methanol in methylene chloride), n.m.r. in deuterated acetone:

δ 5.40–5.57, 2H, multiplet, 5-trans olefin
5.62–5.77, 2H, multiplet, 13-trans olefin
M$^+$ = 659.3494 (calculated for $C_{34}H_{57}NO_6Si_3$ = 659.3483), and the previously-described cis-isomer, $R_F = 0.22$.

The mixture of 5-cis and 5-trans compounds was obtained by the process described in Example 4 for the 5-cis compound, except that the reaction of 4β-dimethoxymethyl-2,3,3aβ,6aβ-tetrahydro-2-hydroxy-5β-(tetrahydropyran-2-yloxy)cyclopenteno[b]furan with (4-carboxybutyl)triphenylphosphonium bromide was carried out using n-butyl-lithium in sulpholane instead of methanesulphinylmethyl sodium in dimethylsulphoxide, to give a mixture of cis and trans isomers. The subsequent intermediates described in Example 4 were then obtained as cis-trans mixtures. Thin layer chromatography of the mixture of 9α,11α,15-trihydroxy-16-(indol-5-yloxy)-17,18,19,20-tetranor-5-cis/trans, 13-trans-prostadienoic acid gave the required mixture of the more polar C-15 epimer 5-cis/trans compounds, $R_F = 0.18$ (3% acetic acid in ethyl acetate) and a mixture of the less polar C-15 epimer 5-cis/trans compounds, $R_F = 0.27$.

EXAMPLE 13

|  | % w/v |
|---|---|
| 9α,11α,15-Trihydoxy-16-(indol-5-yloxy)-17,18,19,20-tetranor-5-cis,13-trans-prostadienoic acid | 0.003 |
| Sodium phosphonate | 2.90 |
| Sodium hydogen phosphate | 0.30 |
| Water for injection | to 100 |

The sodium phosphate was dissolved in about 80% of the water, followed by the prostadienoic acid derivative, and, when dissolved, the sodium hydrogen phosphate. The solution was made up to volume with water for injection, and the pH was checked to be between 6.7 and 7.7. The solution was filtered to remove particulate matter, sterilised by filtration, and filled into pre-sterilised neutral glass ampoules under aseptic conditions. Immediately before use, the contents of an ampoule are diluted in sodium chloride B.P. for administration by infusion.

The prostadienoic acid derivative may, of course, be replaced by an equivalent amount of another prostanoic acid derivative of the invention.

EXAMPLE 14

The process described in Example 4 was repeated, using the appropriate ester in place of ethyl 5-indolyloxy-acetate to give the following compounds:

| R⁴ | Mass Spectrum Found | Mass Spectrum Calculated | Phosphonate $R_F$ | Enone $R_F$ |
|---|---|---|---|---|
| 7-chloroindol-5-yl | 693.3061 | 693.3104⁽ᵃ⁾ | 0.5⁽ᵇ⁾ | 0.5⁽ᶜ⁾ |
| 7-fluoroindol-5-yl | 735.3621 | 735.3640⁽ᵈ⁾ | 0.5⁽ᵇ⁾ | 0.33⁽ᶜ⁾ |
| 6-fluoroindol-5-yl | 807.4024 | 807.4035⁽ᵉ⁾ | 0.3⁽ᵇ⁾ | 0.57⁽ᶜ⁾ |

⁽ᵃ⁾for tri-(trimethylsilyl) methyl ester derivative
⁽ᵇ⁾in ethyl acetate
⁽ᶜ⁾in 20% ethyl acetate in toluene
⁽ᵈ⁾for tetra-(trimethylsilyl) derivative
⁽ᵉ⁾for penta-(trimethylsilyl) derivative

What is claimed is:
1. A prostanoic acid derivative of the formula:

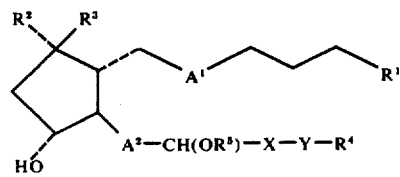

wherein $R^1$ is carboxy or hydroxymethyl, or alkoxycarbonyl of 2 to 5 carbon atoms, $R^2$ is hydroxy and $R^3$ is hydrogen or $R^2$ and $R^3$ together are oxo, $A^1$ is ethylene, cis-vinylene or trans-vinylene, $A^2$ is ethylene or trans-vinylene, X and Y together form methylene, ethylene, methyleneoxy or a direct bond, $R^5$ is hydrogen and $R^4$ is 1-, 2-, 3-, 4-, or 5-indolyl or -indolinyl which bears 0 to 3 substituents selected from halogen, and alkyl and alkoxy each of 1 to 5 carbon atoms, which compound bears 0 or 1 alkyl substituents of 1 or 4 carbon atoms on carbon atom 2 thereof, and the pharmaceutically or veterinarily acceptable base addition salts of those compounds wherein $R^1$ is carboxy.

2. The prostanoic acid derivative of claim 1 wherein $R^4$ is 2-, 3-, 4-, or 5-indolyl, 1-, 3-, or 7-methylindol-5-yl, 1,2-dimethylindol-5-yl, 3-chloroindol-5-yl, 7-fluoroindol-5-yl, 1-indolinyl or 1-methylindolin-5-yl.

3. The prostanoic acid derivative of claim 2 wherein $R^1$ is carboxy, hydroxymethyl or methoxycarbonyl, $A^1$ is ethylene, cis-vinylene or trans-vinylene, $R^2$ is hydroxy, $R^3$ is hydrogen, $A^2$ is ethylene or trans-vinylene, $R^5$ is hydrogen, X is methylene, Y is oxygen, and $R^4$ is 5-indolyl, or 7-fluoroindol-5-yl, and for those compounds wherein $R^1$ is carboxy, the sodium and potassium salts thereof.

4. The prostanoic acid derivative of claim 2 which is selected from 9α,11α,15-trihydroxy-16-(indol-5-yloxy)-17,18,19,20-tetranor-5-cis, 13-trans-prostadienoic acid, 16-(7-fluoroindol-5-yl)-9α,11α,15-trihydroxy-17,18,19,20-tetranor-5-cis,13-trans-prostadienoic acid, methyl 9α,11α,15-trihydroxy-16-(indol-5-yloxy)-17,18,19,20-tetranor-5-cis,13-trans-prostadienoate, 16-(indol-5-yloxy)-17,18,19,20-tetranor-5-cis,13-trans-prostadien-1,9α,11α,15-tetra-ol, 9α,11α,15-trihydroxy-16-(indol-5-yloxy)-2-methyl-17,18,19,20-tetranor-5-cis,13-trans-prostadienoic acid, 9α,11α,15-trihydroxy-16-(indol-5-yloxy)-17,18,19,20-tetranor-13-trans-prostenoic acid, 9α,11α,15-trihydroxy-16-(indol-5-yloxy)-17,18,19,20-tetranor-5-trans, 13-trans-prostadienoic acid, 9α,11α,15-trihydroxy-17-(indolin-1-yl)-18,19,20-trinor-5-cis,13-trans-prostadienoic acid and 9α,11α,15-trihydroxy-16-(1-methylindolin-5-yloxy)-17,18,19,20-tetranor-5-cis,13-trans-prostadienoic acid, and the sodium and potassium salts of those compounds which are acids.

5. The prostanoic acid derivative of claim 1 which is 16-(7-fluoroindol-5-yloxy)-9α,11α,15-trihydroxy-17,18,19,20-tetranor-5-cis,13-trans-prostadienoic acid.

6. The prostanoic acid derivative of claim 1, which is 9α,11α,15-trihydroxy-16-(indol-5-yloxy)-17,18,19,20-tetranor-5-cis, 13-trans-prostadienoic acid.

7. A pharmaceutical or veterinary composition consisting essentially of the prostanoic acid derivative of claim 1 in association with a major amount of a pharmaceutically or veterinarily acceptable diluent or carrier therefor.

* * * * *